United States Patent
Maine et al.

(10) Patent No.: US 7,432,046 B2
(45) Date of Patent: Oct. 7, 2008

(54) METHODS FOR THE DETERMINATION OF ANTIBODY IGG AVIDITY

(75) Inventors: Gregory T. Maine, Gurnee, IL (US); Stephen C. Hsu, Buffalo Grove, IL (US); Darwin D. Smith, Gurnee, IL (US); Dominick L. Pucci, Libertyville, IL (US); Jörg Herzogenrath, Hünstetten-Limbach (DE); Ingo Curdt, Hochheim am Main (DE); Heike Maria Christ, Waldbrunn (DE)

(73) Assignee: Abbott Laboratories, Abbott Park, IL (US)

( * ) Notice: Subject to any disclaimer, the term of this patent is extended or adjusted under 35 U.S.C. 154(b) by 51 days.

(21) Appl. No.: 11/265,481

(22) Filed: Nov. 2, 2005

(65) Prior Publication Data

US 2007/0099295 A1    May 3, 2007

(51) Int. Cl.
| | |
|---|---|
| G01N 33/543 | (2006.01) |
| G01N 33/553 | (2006.01) |
| G01N 33/552 | (2006.01) |
| G01N 33/544 | (2006.01) |
| G01N 33/546 | (2006.01) |
| G01N 33/53 | (2006.01) |
| G01N 33/00 | (2006.01) |
| C12Q 1/70 | (2006.01) |

(52) U.S. Cl. ............... 435/5; 436/523; 436/526; 436/527; 436/528; 436/533; 436/518; 435/5; 435/7.1; 435/7.22; 435/7.93

(58) Field of Classification Search ............... None
See application file for complete search history.

(56) References Cited

U.S. PATENT DOCUMENTS

| | | | |
|---|---|---|---|
| 5,705,330 | A | 1/1998 | Shah et al. |
| 6,074,817 | A | 6/2000 | Landini et al. |
| 6,329,157 | B1 * | 12/2001 | Maine et al. ............... 435/7.22 |
| 6,372,426 | B1 | 4/2002 | Zens |
| 7,094,879 | B2 | 8/2006 | Maine et al. |

FOREIGN PATENT DOCUMENTS

| | | |
|---|---|---|
| EP | 0 431 541 | 4/1990 |
| EP | 0 751 147 | 4/1990 |

OTHER PUBLICATIONS

Makarananda, et al. Competitive ELISA. In: Methods in Molecular Biology, vol. 80: Immunochemical Protocols, 2nd ed. Edited by: J.D. Pound. © 1998, Humana Pres Inc., Totowa, NJ. p. 155-160.*

(Continued)

*Primary Examiner*—Mary R. Mosher
*Assistant Examiner*—Stuart W. Snyder
(74) *Attorney, Agent, or Firm*—Cheryl L. Becker; Audrey L. Bartnicki

(57) ABSTRACT

The present invention relates to methods of determining anti-infectious agent IgG avidity, for example, human anti-cytomegalovirus and human anti-toxoplasma IgG avidity, using a competitive assay format.

12 Claims, 2 Drawing Sheets

OTHER PUBLICATIONS

Sager, et al. Immunodiagnosis of primary Toxoplasma gondii infection in sheep by the use of a p30 IgG ELISA. Parasitol Res (2003) 91:171-174.*

Just-Nubling, et al. Primary cytomegalovirus infection in an outpatient setting—laboratory markers and clinical aspects. Infection (Germany) Oct. 2003, 31 (5) p. 318-23.*

Abou-Basha, L.M., et al., "Specific IgG avidity in acute and chronic human fascioliasis", *East. Mediterr. Health J.*, 6:919-925 (2000).

Baccard-Longere, M., et al., "Multicenter Evaluation of a rapid and Convenient Mehtod for Determination of Cytomegalovirus Immunoglobulin G Avidity", *Clin. & Diag. Lab. Immun.*, 8(2):429-431 (2001).

Benjamin, P.A., et al., "Increased titre and avidity of IgG antibodies to *Porphyromonas gingivalis* whole cells and a cell surface protein in subjects with adult periodontitis", *J. Period.. Res.*, 32:31-39 (1997).

Bodeus, M., et al., "Avidity of IgG antibodies distinguishes primary from non-primary cytomegalovirus infection in pregnant women", *Clin, And Diag. Virol.*, 9:9-16 (1998).

Bonhomme, A., et al., "Quantitative Immunolocalization of a P29 Protein (GRA7), a New Antigen of Toxoplasma gondii", *J. of Histochem. & Cytochem.*, 46(12):1411-1421 (1998).

Boppana, S.B., et al., "Symptomatic congenital cytomegalovirus infection: neonatal morbidity and mortality", *Pediatr. Infect. Dis. J.*, 11(2):93-99 (1992).

Boppana, S.B., et al., "Symptomatic Congenital Cytomegalovirus Infection in Infants Born to Mothers With Preexisting Immunity to Cytomegalovirus", *Pediatrics*, 104:55-60 (1999).

Britt, W.J. & Alford, C.A., "Cytomegalovirus", *Cytomegalovirus, In Fields Virology*, 3rd Ed., Chapt. 77:2493-2523 (1996).

Burg, J.L., et al., Molecular Analysis of the Gene Encoding the Major Surface Antigen of *Toxoplasma gondii* J. of Immunol., 141(10):3584-3591 (1988).

Carey, K.L., et al., "Identification and molecular characterization of GRA8, a novel, proline-rich, dense granule protein of *Toxoplasma gondii*", *Molec. & Biochem Parasitology*, 105:25-37 (2000).

Cesbron-Delauw, M.F., et al., "Molecular characterization of a 23-kilodalton major antigen secreted by *Toxoplasma gondii*", *Proc. Natl. Acad. Sci., USA*, 86:7537-7541 (1989).

Chan, P.K.S., et al., "Antibody Avidity Maturation during Severe Acute Respiratory Syndrome-Associatd Coronavirus Infection",*J. Infect. Dis.*, 192:166-169 (2005).

Chee, M.S., et al., "Analysis of the Protein-Coding Content of the Sequence of Human Cytomegalovirus Strain LAD169", *Curr. Top. Microbiol. Immuno.*, 154:125-169 (1990).

Devash, Y., et al., "Vertical transmission of human immunodeficiency virus is correlated with the absence of high-affinity/avidity maternal antibodies to the gp120 principal neutralizing domain", *Proc. Natl. Acad. Sci., USA*, 87:3455-3449 (1990).

Devey, M.E., et al., "Determination of the functional affinity of IgG1 and IgG4 antibodies to tetanus toxoid by isotype-specific solid-phase assays", *J. of Immunol. Meth.*, 106:119-125 (1988).

De Souza, V.K.U.F., et al., "Use of an Immunoglobulin G Avidity Test To Discriminate between Primary and Secondary Dengue Virus Infections", *J. of Clin. Microbiol.*, 42(4):1782-1784 (2004).

Gassmann, C. & Bauer, G., "Avidity Determination of IgG Directed Against Tick-Borne Encephalitis Virus Improves Detection of Current Infections",*J. of Med. Virol.*, 51:242-251 (1997).

Gray, J.J. et al., "Detection of human parvovirus B19-specific IgM and IgG antibodies using a recombinant virual VP1 antigen expressed in insect cells and estimation of time of infection by testing for antibody avidity",*J. of Virol. Meth.*, 44:11-24 (1993).

Gutierrez F. J., et al., "Relaciórrez entrée el tiempo de evolución de la brcelosis humana y la avidez de anticuerpos IgG especificos", *Revista Medica de Chile*, 123:819-822 (1995).

Halliday, G.M., et al., "Evaluation of an ELISA system for determination of class-specific antibodies to antive and denatured DNA in man", *Annals of the Rheumatic Dis.*, 44:507-513 (1985).

Hedman, K. & Seppala, I., "Recent Rubella Virus Infection Indicated by a Low Avidity of Specific IgG",*J. of Clin. Immunol.*, 8(3):214-221 (1988).

Hedman, K., et al., "Recent Primary Toxoplasma Infection Indicated by a Low Avidity of Specific IgG", *J. Infect. Dis.*, 159(4):736-740 (1989).

Hedman, K. & Rousseau S.A., "Measurement of Avidity of Specific IgG for Verification of Recent Primary Rubella", *J. of Med. Virol.*, 27:288-292 (1989).

Hedman, K., et al., "Rapid diagnosis of hantavirus disease with an IgG-avidity assay", *The Lancet*, 338:1343-1356 (1991).

Inouye, S., et al., "Changes in Antibody Avidity After Virus Infections: Detection by an Immunosorbent Assay in Which a Mild Protein-Denaturing Agent Is Employed",*J. of Clin. Microbiol.*, 20*3):525-529 (1984).

Johnson, A.M. & Illana, S., "Cloning of *Toxoplasma gondii* gene fragments encoding diagnostic antigens", *Gene*, 99:127-132 (1991).

Kaukonen, K., et al., "Avidity of *Aspergillus umbrosus* IgG antibodies in farmer's lung disease", *Clin. Exp. Immunol.*, 95:162-165 (1994).

Lappalainen, M., et al., "Toxoplasmosis Acquired during Pregnancy: Improved Serodiagnosis Based on Avidity of IgG",*J. Infect. Dis.*, 167:691-697 (1993).

Lazzarotto, T., et al., "Enzyme-Linked Immunoadsorbent Assay for the Detection of Cytomegalovirus IgM: Comparison Between Eight Commercial Kits, Immunofluorescence, and Immunoblotting",*J. of Clin. Lab. Analy.*, 6:216-218 (1992).

Lehner, R., et al., "Comparative Sequence Analysis of Human Cytomegalovirus Strains",*J. of Clin. Microbiol.*, 29(11):2494-2502 (1991).

Liesenfeld, O., et al., "False-Positive Results in Immunoglobulin M (IgM) Toxoplasma Antibody Tests and Importance of Confirmatory Testing: the Platelia Toxo IgM Test",*J. of Clin. Microbiol.*, 35(1):174-178 (1997).

Maine, G., et al., "New Developments in the diagnosis of maternal and congenital CMV infection", *Expert Rev. Mol. Diagn.*, 1(1):29-29 (2001).

Mevelec, M-N., et al., "Molecular cloning of GRA4, a *Toxoplasma gondii* dense granule protein, recognized by mucosal IgA antibodies", *Molec. & biochem. Parasitol.*, 56:227-238 (1992).

Montoya, J.G., et al., "VIDAS Test for Avidity of *Toxoplasma*-Specific Immunoglobulin G for Confirmatory Testing of Pregnant Women",*J. of Clin. Microbiol.*, 40(7):2504-2508 (2002).

Morrow, R.A., et al., "Development and Use of a Type-Specific Antibody Avidity Test Based on Herpes Simplex Virus Type 2 Glycoprotein G",*Sexual. Transmitt. Dis.*, 31(8):508-515 (2004).

Mostafa, N.E., et al., "Low Avidity IGG Antibodies in Diagnosis of Recent Human Schistosimiasis",*J. of the Egyptian Soc. Of Parasitol.*, 32(3):979-985 (2002).

Naot, Y. & Remington, J.S., "An Enzyme-Linked Immunosorbent Assay for Detection of IgM Antibodies to *Toxoplasma gondii*: Use for Diagnosis of Acute Acquired Toxoplasmosis",*J. of Inf. Dis.*, 142(5):757-766 (1980).

Nielsen, S.L., et al., "Kinetics of Specific Immunoglobulins M, E, A, and G in Congenital, Primary, and Secondary Cytomegalovirus Infection Studied by Antibody-Capture Enzyme-Linked Immunosorbent Assay",*J. of Clin. Microbiol.*, 26(4):654-661 (1988).

O'Dell, D.S. & Ebersole, J.L., "Avidity of antibody responses to *Actinobacillus actinomycetemcomitans* in periodontitis", *Clin. Exp. Immunol.*, 101:295-301 (1995).

Ono, E., et al., "A Simple and Cheaper in House Varicella Zoster irus Antibody Indirect Elisa", *Rev. Inst. Med. Atrop. S. Paulo*, 46(3):165-168 (2004).

Petersen, E., et al., "European Multicenter Study of the LIAISON Automated Diagnostic System for Determination of *Toxoplasma gondii*-Specific Immunoglobulin G (IgG) and IgM and the IgG Avidity Index",*J. of Clin. Microbiol.*, 43(4):1570-1574 (2005).

Pfrepper, K.-l., et al., "Seroreactivity to and Avidity for Recombinant Antigens in Toxoplasmosis",*Clin. & Diag. Lab. Immunol.*, 12(8):977-982 (2005).

Prince, J.B., et al., "Cloning of cDNAs encoding a 28 kilodalton antigen of *Toxoplasma gondii*", *Molec. & Biochem. Parasitol.*, 34:3-13 (1989).

Prince, J.B., et al., "Cloning, expression, and cDNA sequence of surface antigen P22 from *Toxoplasma gondii*", 43:97-106 (1990).

Rauer, S., et al., "Avidity Determination of Borrelia burgdorferi-specific IgG Antibodies in Lyme Disease",*Scand. J. Infect. Dis.*, 33:809-811 (2001).

Reiter-Owona, I., "The past and present role of the Sabin-Feldman dye test in the serodiagnosis of toxoplasmosis", *Bull. Of the Wrld. Health Org.*, 77(11):929-935 (1999).

Remington & Klein, *Infectious Diseases of the Fetus and Newborn Infant*, 5th Ed.:140-267 (2001).

Roque-Afonso, A.-M., et al., "Diagnostic Relevance of Immunoglobulin G Avidity for Hepatitis A Virus",*J. of Clin. Microbiol.*, 42(11):5121-5124 (2004).

Saavdra, R., et al., "Human T Cell Clone Identifies a Potentially Protective 54-kDa Protein Antigen of *Toxoplasma gondii* Cloned and Expressed in *Escherichia coli*", *J. of Immunol.*, 147(6):1975-1982 (1991).

Sabin, A.B. & Feldman, H.A., "Dyes as Microchemical Indicators of a New Immunity Phenomenon Affecting a Protozoon Parasite (Toxoplasma)[1]", *Science*, 108:660-663 (1948).

Jacobs, L. & Lunde, M.N., "A Hemagglutination Test for Toxoplasmosis",*J. Parasitol.* 43:308-314 (1957).

Stagno, S., *Infectious Diseases of the Fetus & Newborn Infant*, 4th Ed.:313-353 (1995).

Suligoi, B., et al. "Precision and Accuracy of a Procedure for Detecting Recent Human Immunodeficiency Virus Infections by Calculating the Antibody Avidity Index by an Automated Immunoassay-Based Method", *J. of Clin. Microbiol.*, 40(11):4015-4020 (2002).

Thomas, H.I.J., "Relative Functional Affinity of Specific Anti-Core IgG in Different Categories of Hepatitis B Virus Infection",*J. of Med. Virol.*, 51:189-197 (1997).

Thomas, H.I.J. & Morgan-Capner, P., "Rubella-specific IgG subclass avidity ELISA and its role in the differntiation between primary rubella and rubella reinfection", *Epidem. Inf.*, 101:591-598 (1988).

Thomas, H.I.J., & Morgan-Capner, P., "Rubella-specific $IgG_1$ avidity: a comparison of methods", *J. of Virol. Meth.*, 331:219-228 (1991).

Trincado, D.E., et al., "Human Cytomegalovirus Strains Associated With Congenital and Perinatal Infections",*J. of Med. Virol.*, 61:481-487 (2000).

Villaita, D., et al., "Evaluation of a New Automoated Enzyme Fluoroimmunoassay Using Recombinant Plasmid dsDNA for the Detection of Anti-dsDNA Antibodies in SLE",*J. of Clin. Lab. Analy.*, 16:227-232 (2002).

Villalta, D., et al., "Anti-dsDNA antibody avidity determination by a simple reliable ELISA method for SLE diagnosis and monitoring", *Lupus*, 12:31-36 (2003).

Walton, B.C., et al., "Comparison of the Indirect Fluorescent Antibody Test and Methylene Blue Dye Test for Detection of Antibodies to *Toxoplasma gondii*", *Amer. J. Trop. Med. & Hygiene*, 15(2):149-152 (1966).

Ward, K.N., et al., "Measurement of Antibody Avidity for Hepatitis C Virus Distinguishes Primary Antibody Responsis From Passively Acquired Antibody",*J. of Med. Virol.*, 43:367-372 (1994).

Ward, K.N., et al., "Use of Immunoglobulin G Antibody Avidity for Differentiation of Primary Human Herpesvirus 6 and 7 Infections", *J. of Clin. Microbiol.*, 39(3):959-963 (2001).

Weissbrich, B., "The Use of Semi-Automated EBV IgG Avidity Determination for the Diagnosis of Infectious Mononucleosis", *J. of Med. Virol.*, 54:145-153 (1998).

Wilson, M., et al., "Evaluation of Six commercial Kits for Detection of Human Immunoglobulin M Antibodies to *Toxoplasma gondii*", *J. of Clin. Microbiol.*, 35(12):3112-3115 (1997).

Wong, S.-Y. & Remington, J.S., "Toxoplasmosisin Pregnancy", *Clin. Inf. Dis.*, 18:853-862 (1994).

Zhang, J.-Z., et al., "Occurrence of Hepatitis E Virus IgM, Low Avidity IgG Serum Antibodies, and Viremia in Sporadic Cases of Non-A, -B, and -C Acute Hepatitis",*J. of Med. Virol.*, 66:40-48 2002).

Lazzarotto, T, et aal, "Evaluation of the Abbott AxSYM Cytomegalovirus (CMV) Immunoglobulin M (IgM) Assay in Conjunction with Other CMV IgM Tests ad a CMV IgG Avidity Assay", Clin & Diag Lab Immunol, 8(1):196-198 (2001).

Villalta et al. (2002) J. Clin. Laboratory Analysis 16:227-232 entitled "Evaluation of a New Automated Enzyme Fluroimmunoassay Using Recombinant Plasmid dsDNA for the Detection of Anti-dsDNA antibodies in SLE".

Friguet et al. (1985) Journal of Immunological Methods 77:305-319 entitled "Measurements of the True Affinity Constant in Solution of Antigen-Antibody Complexes by Enzyme-Linked Immunosorbent Assay".

* cited by examiner

METHODS FOR THE DETERMINATION OF ANTIBODY IGG AVIDITY

BACKGROUND OF THE INVENTION

Technical Field

The present invention relates to methods of determining anti-infectious agent IgG antibody avidity, for example, human anti-cytomegalovirus and human anti-toxoplasma IgG antibody avidity.

BACKGROUND INFORMATION

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140-267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites, which can infect the individual resulting in an acute infection. Oocysts represent a stage of sexual reproduction, which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudesence of a previous *T. gondii* infection or an acute infection in an immunosuppressed individual can be pathogenic. Toxoplasmic encephalitis is a major cause of morbidity and mortality in AIDS patients. Toxoplasma infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660-663), the indirect hemagglutination (IHA) test (Jacobs, L. and Lunde, M. (1957) J. Parasitol. 43, 308-314), the IFA test (Walton, B. C. et al. (1966) Am. J. Trop. Med. Hyg. 15, 149-152), the agglutination test (Fondation Mérieux, Sérologie de l'Infection Toxoplasmique en Particulier à Son Début: Méthodes et Interprétation des Résultants, Lyon, 182 pp. (1975)) and the ELISA (Naot, Y. and Remington, J. S. (1980) J. Infect. Dis. 142, 757-766). The ELISA test is one the easiest tests to perform, and many automated serologic tests for the detection of Toxoplasma specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice, which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, as described above, as well as the persistent problems regarding determination of onset of infection, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P29 (GRA7), P30 (SAG1), P35 (GRA 8), P41 (GRA4), P54 (ROP2), P66 (ROP1), and the Toxo P68 antigens have been described (Prince et al. (1990) Mol. Biochem. Parasitol 43, 97-106; Cesbron-Delauw et al. (1989) Proc. Nat. Acad. Sci. 86, 7537-7541; Johnson et al. (1991) Gene 99, 127-132; Prince et al. (1989) Mol. Biochem. Parasitol. 34, 3-13; Bonhomme et al. (1998) J. Histochem. Cytochem. 46, 1411-1421; Burg et al. (1988) J. Immunol. 141, 3584-3591; Knapp et al. (1989) EPA 431541A2; Carey et al. (2000) Molec. Biochem. Parasitol. 105, 25-37; Mevelec et al. (1992) Mol. Biochem. Parasitol. 56, 227-238; Saavedra et al. (1991) J. Immunol. 147, 1975-1982); EPA 751 147).

Additionally, it should be noted that the presence of IgG antibodies in a single sample of serum is sufficient to establish that the patient has been infected but does not give an indication as to when the infection occurred. However, in the United States, there is no systematic serological screening program in pregnant women, whereas in countries such as France and Austria, sera are obtained at regular intervals throughout gestation in women who are seronegative when first tested. In the United States, a decision regarding whether the woman was recently infected, thereby placing her fetus at risk, is often made from results in a single sample of serum. However, it is critical in pregnant women to determine as accurately as possible if they acquired their infection just prior to or during gestation. For this reason, the presence of IgG antibodies in a pregnant woman often leads to additional serological testing to attempt to determine if the infection was acquired during pregnancy or in the distant past (Remington et al., 1995, Toxoplasmosis, 4th ed., Coord. Ed., Remington, J. S., W. B. Saunders, Philadelphia, Pa.). Of the recommended additional serological tests, those that demonstrate the presence of IgM antibodies are most frequently used. However, since IgM antibodies may remain detectable for more than one year after initial infection, demonstration of these antibodies cannot be used to prove recently acquired infection (Liesenfeld et al., *Journal of Clinical Microbiology* 35:174-78 (1997); Wilson et al., *Journal of Clinical Microbiology* 35:3112-15 (1997); Wong et al., *Clinical Infectious Diseases* 18:853-62 (1994)).

Because accurate diagnosis of the recently acquired infection in pregnant women is important for clinical management of both the mother and her fetus, a search has continued for better diagnostic methods (Remington et al., 1995, Toxoplasmosis, 4$^{th}$ ed., Coord. Ed., J. S. Remington, W. B. Saunders, Philadelphia, Pa.; Wong et al., supra).

Human Cytomegalovirus (HCMV) is a member of the group of herpes viruses, is a ubiquitous agent, and is responsible for a broad spectrum of disease affecting humans in many different clinical settings. It is rarely pathogenic in healthy adults but is associated with several diseases in immunocompromised individuals (such as HIV-infected people and transplant recipients). Furthermore, HCMV is the most common cause of congenital infection, occurring in approximately 1% of all live births (Britt, W. J. and Alford, C. A. (1996) Cytomegalovirus, In Fields Virology, 3$^{rd}$ ed., Fields et al. (eds.), Lippincott-Raven Publishers, Philadelphia, Pa., 2493-2523; Stagno, S. (1995) Cytomegalovirus. In Infectious Diseases of the Fetus and Newborn Infant (4$^{th}$ ed.) Remington, J. S. and Klein, J. O. (eds.), W. B. Saunders, Philadelphia, Pa., 312-353). Since HCMV infections in pregnant women are asymptomatic or accompanied by non-specific symptoms, laboratory methods including serology and virology are used to diagnose HCMV infection.

Diagnosis of HCMV infection can be obtained by direct demonstration of the virus in various body fluids or indirectly through serology. In order for the physician to accurately assess the risk of a pregnancy potentially complicated by maternal HCMV infection, it is important to distinguish between primary and non-primary HCMV infection. Intrauterine transmission of primary HCMV infection (ca. 40%) in the first trimester of pregnancy has the potential to cause significant fetal damage, including fetal death (Boppana, S. et al. (1992) Pediatr. Infect. Dis. J. 11,93-99). Intrauterine transmission of non-primary HCMV infection occurs at a much lower rate (ca. 0.2-1%) and is generally but not always asymptomatic in the developing newborn (Boppana, S. et al. (1999) Pediatr. 104,55-60).

The diagnosis of primary HCMV infection in patients is confirmed if seroconversion to HCMV-specific IgG and IgM antibodies is detected. However, since there are currently no treatment options available for primary HCMV infection in pregnant women, seroconversion to HCMV-specific antibodies is detected rarely as pre-gestational, and pregnant women are not routinely screened for HCMV antibodies. The detection of HCMV-specific IgM has been used as a marker of active or recent HCMV infection (Nielsen, S. L. (1988) J. Clin. Microbiol. 26,654-661) and its detection varies widely with poor agreement among commercial tests (Lazzarotto, T. et al. (1992) J. Clin. Lab. Anal. 6,216-218). Unfortunately, HCMV-specific IgM can be produced during both primary and non-primary HCMV infections, and hence this test serves only as a marker to flag pregnancies at risk for potential congenital HCMV infection that require additional clinical testing and follow-up.

Serological tests for the detection of Toxo-specific IgM antibodies and HCMV-specific IgM antibodies in pregnant women serve as markers for pregnancies at risk for congenital infection. However, these tests are not able to discriminate between an acute and chronic toxoplasmosis or a primary and non-primary HCMV infection, respectively. Since an acute maternal toxoplasmosis or a primary maternal HCMV infection during the first trimester poses the greatest risk for fetal damage, additional testing is required to more accurately assess the risk and potential impact the maternal infection has on the developing fetus and newborn. In particular, a test is needed which can aid in the determination of whether the maternal infection was acquired during gestation or whether the infection occurred sometime in the distant past, i.e., prior to conception. If the infection occurred prior to conception, maternal immunity would be sufficient to protect the developing fetus in utero and no further testing or intervention would be required. On the other hand, if the infection occurred during gestation, obstetric counseling would be given to pregnant women and in the case of a suspected acute toxoplasmosis, therapeutic intervention could begin to attempt to prevent intrauterine transmission of the parasite.

It is known that the functional binding affinity or avidity of IgG antibodies increases progressively with time after immunization of animals, also known as maturation of the humoral immune response (Inouye at al. (1984) J. Clin. Microbiol. 20, 525-529). Conventional affinity assays, for example, equilibrium dialysis using Scatchard analysis, are not suitable for the measurement of the polyclonal responses elicited by large and complex microbial, viral and parasitic antigens (Hedman, K. and Rousseau, S. A. (1989) J. Virol. 27, 288-292). Competitive binding assays have been used to assess antibody affinity following vaccination and maternal protective immunity to congenital HIV infection (Devey, M. E. et al. (1988) J. Immunol. Methods 106, 119-125; Devash, Y. et al. (1990) Proc. Nat. Acad. Sci. USA 87, 3445-3449). However, competitive binding assays have not been described that discriminate between an acute infection and an infection acquired in the distant past.

Further, it is well established that IgG avidity assays utilizing chaotropic reagents can be used at the diagnostic level to discriminate between an acute infection (low avidity IgG antibodies predominantly present) and an infection acquired in the distant past (high avidity IgG antibodies predominantly present) for a variety of infectious agents including HCMV (Bodéus, M. et al. (1998) Clin. Diagn. Virol. 9, 9-16), *T. gondii* (Lappalainen, M. et al.(1993) J. Infect. Dis. 167, 691-697), Human Immunodeficiency Virus (HIV) (Suligoi, B. et al. (2002) J. Clin. Microbiol. 40, 4015-4020), Parvovirus B19 (Gray, J.J. et al. (1993) J. Virol. Meth. 44, 11-23), Herpesvirus 6 and 7 (Ward, K. N. et al. (2001) J. Clin. Microbiol. 39, 959-963), Hepatitis A, B, C, E virus (Roque-Afonso, A. -M. et al. (2004) J. Clin. Microbiol. 42, 5121-5124; Thomas, H. I. J. (1997) J. Med. Virol. 51, 189-197; Ward, K. N. et al. (1994) J. Med. Virol. 43, 367-372; Zhang, J. -Z. et al. (2002) J. Med. Virol. 66, 40-48), Epstein-Barr Virus (EBV) (Weissbrich, B. (1998) J. Med. Virol. 54, 145-153), Actinobacillus actinomycetemcomitans (juvenile periodontis) (O'Dell, D. S. et al. (1995) Clin. Exp. Immunol. 101, 295-301), Herpes Simplex Virus Type 2 (Ashley, R. et al. (2004) Sexual. Transmitt. Dis. 31, 508-515), Severe Acute Respiratory Syndrome (SARS) (Chan, P. K. S. et al. (2005) J. Infect. Dis. 192, 166-169), Fascioliasis (liver flukes) (Abou-Basha, L. M. et al. (2000) East. Mediterr. Health J. 6, 919-925), Tick-Borne Encephalitis Virus (TBEV) (Gassman, C. G. and Bauer, G. (1997) J. Med. Virol. 51, 242-251), Rubella (Hedman, K. and Rousseau, S. A. (1989) J. Med. Virol. 27, 288-292), Lyme borreliosis (Rauer, S. et al. (2001) Scand. J. Infect. Dis. 33, 809-811), Varicella Zoster Virus (VZV) (Erika, O. (2004) Revista do Instituto de Medicina Tropical de Sao Paulo 46, 165-168), Dengue Virus (Fick, de Souza V. A. U. et al. (2004) J. Clin. Microbiol. 42, 1782-1784), Schistosomiasis (blood flukes) (J. Egypt. Soc. Parasitol. 32, 979-985), Porphyromonas gingivalis (periodontis) (Benjamin, P. A. et al. (1997) J. Period. Res. 32,31-39), *Aspergillus umbrosus* (farmer's lung disease) (Clin. Exp. Immunol. 95, 162-165), Puumala Virus (Hedman, K. et al. (1991) Lancet 338, 1353-1356), and Brucellosis (Gutierrez, J. et al. (1995) Revista Medica de Chile 123, 819-822). Current "home brew" and commercial IgG avidity assays employ the use of chaotropic reagents (e.g., urea, diethylamine, thiocyanate, guanidium, etc.) to distinguish between antibodies of high and low avidity (see U.S. Pat. No. 6,372,426B1; Hedman, K. and Seppala, I. (1988) J. Clin. Immunol. 8, 214-221; Hedman et al. (1989) J. Infect. Dis. 4, 736-740; Thomas, H. I. J. and Morgan-Capner, P. (1988) Epidem. Inf. 101, 591-598; Thomas, H. I. J. and Morgan-Capner, P. (1991) J. Virol. Methods 31, 219-228; Montoya, J. G. et al. (2002) J. Clin. Microbiol. 40, 2504-2508; Pfrepper, K. -I. et al. (2005) Clin. Diagn. Labora. Immunol. 12, 977-982; Petersen, E. et al. (2005) J. Clin. Microbiol. 43, 1570-1574; Baccard-Longere, M. et al. Clin. Diagn. Labora. Immunol. 8, 429-431). The chaotropic reagent can be added to the patient sample to inhibit the binding of low avidity antibodies to the "solid phase antigen" during incubation with the "solid phase antigen". Alternatively, the chaotropic agent can be used to wash the "solid phase antigen" after incubation of the patient sample with the "solid phase antigen". Low avidity IgG antibodies are then stripped from the "solid phase antigen" by the chaotropic reagent. The ratio of the signal in the avidity assay is determined with an anti-human IgG conjugate containing a signal-generating compound in the presence and in the absence of the chaotropic reagent (added either to the sample or used to wash the "solid phase antigen") and is proportional to the level of high avidity IgG present in the patient sample. However, chaotropic reagents can be hazardous or corrosive to an automated immunoassay instrument platform and may also cross-contaminate other assays thereby causing aberrant results. Consequently, there is a current and significant need for an automated IgG avidity immunoassay that does not utilize chaotropic reagents.

All patents and publications referred to herein are hereby incorporated in their entirety by reference.

SUMMARY OF THE INVENTION

The present invention includes a method of determining the level of human anti-infectious agent IgG antibody avidity in a patient suspected of having been infected by the infectious agent. This method comprises the steps of: a) adding at least one purified antigen from the infectious agent to a solution to create a liquid phase antigen and coating the at least one purified antigen onto a solid phase to create a solid phase antigen; b) in a first assay, contacting a test sample from the patient with a liquid phase comprising no infectious antigen and contacting a test sample from the patient with the coated solid phase of step a) for a time and under conditions sufficient for formation of antibody/antigen complexes; c) washing the coated solid phase of step b); d)in a second assay, contacting a test sample from the patient with the liquid phase antigen and contacting a test sample from the patient with the solid phase antigen for a time and under conditions sufficient for formation of antibody/antigen complexes; e) washing the contacted solid phase antigen of step d); f)adding a conjugate to the first and second assays for a time and under conditions sufficient for formation of anti-IgG/antibody/antigen complexes in the first and second assays, wherein the conjugate comprises an anti-IgG antibody attached to a signal-generating compound capable of generating a detectable signal; g) detecting a signal generated by the signal-generating compound in the first and second assay; and h) determining the ratio between the signal obtained in the second assay to the signal obtained in the first assay, wherein the ratio is proportional to the level of human anti-infectious agent low avidity IgG antibody present in the patient. The infectious agent may be, for example, a virus, a parasite, a fungus or a bacteria. Further, the patient sample may be pretreated with solution prior to addition of the coated solid phase. Also, the solid phase may be, for example, a porous material, a non-porous material, a latex particle, a magnetic particle, a microparticle, a bead, a membrane, a microtiter well or a plastic tube.

Further, the present invention encompasses a method of determining the level of human anti-toxoplasma low avidity IgG antibody in a patient. This method comprises the steps of: a) adding at least one purified antigen from *Toxoplasma gondii* (*T. gondii*) to a solution (e.g., diluent) to create a liquid phase antigen and coating the at least one purified antigen onto a solid phase to create a solid phase antigen; b) in a first assay, contacting a test sample from the patient with a liquid phase comprising no *T. gondii* antigen and contacting a test sample from the patient with the coated solid phase of step a) for a time and under conditions sufficient for formation of antibody/antigen complexes; c) washing the coated solid phase of step b); d) in a second assay, contacting a test sample from the patient with the liquid phase antigen and contacting a test sample from the patient with the solid phase antigen for a time and under conditions sufficient for formation of antibody/antigen complexes; e) washing the contacted solid phase antigen of step d); f) adding a conjugate to the first and second assays for a time and under conditions sufficient for formation of anti-IgG/antibody/antigen complexes in the first and second assays, wherein the conjugate comprises an anti-IgG antibody attached to a signal-generating compound capable of generating a detectable signal; g) detecting a signal generated by the signal-generating compound in the first and second assays; and h) determining the ratio between the signal obtained in the second assay to the signal obtained in the first assay, wherein the ratio is proportional to the level of human anti-Toxo low avidity IgG antibody present in the patient. This method may further comprise the step of: i) multiplying the ratio of step h) by 100 and subtracting the multiplied ratio from 100 in order to determine an Avidity Index, an Avidity Index of <30% indicating the patient has low avidity Toxo IgG, an Avidity Index of ≧40% indicating the patient has high avidity Toxo IgG, and an Avidity Index of 30% to 39% indicating the patient is equivocal for Toxo IgG antibody avidity. Alternatively, the method may further comprise the step of multiplying the ratio of step h) by 100 and subtracting the multiplied ratio from 100 in order to determine an Avidity Index, an Avidity Index of <20% indicating said patient has low avidity Toxo IgG, an Avidity Index of ≧50% indicating said patient has high avidity Toxo IgG, and an Avidity Index of 20% to 49% indicating said patient is equivocal for Toxo IgG antibody avidity. (An "equivocal" result is one that is uncertain and necessitates that another sample be taken from the patient (e.g., 2-3 weeks subsequent to the first test) and tested using the methods described herein. It is neither a low or high avidity IgG result. Further, an "equivocal" result may also be referred to as a "borderline", "grayzone", "mean" or "moderate" result.) A low avidity Toxo IgG result indicates the patient may or may not have acute toxoplasmosis, and a high avidity Toxo IgG result indicates the patient has not had acute toxoplasmosis within approximately 4 months prior to testing.

The "at least one purified antigen" in the method may be, for example, P22, P24, P25, P28, P29, P30, P35, P41, P54, P66 and P68. (The purified or isolated antigen may be created by recombinant means, by synthetic means or extracted from *T. gondii* subsequent to transcription and translation of the organism's genome.) Further, the patient test sample may be pretreated with solution prior to addition of the coated solid phase. Again, the solid phase may be, for example, a porous material, a non-porous material, a latex particle, a magnetic particle, a microparticle, a bead, a membrane, a microtiter well or a plastic tube.

Additionally, the present invention includes a method of determining the level of human anti-cytomegalovirus IgG antibody avidity in a patient. This method comprises the steps of: a) adding at least one purified antigen from human cytomegalovirus (HCMV) to a solution to create a liquid phase antigen and coating the at least one purified antigen onto a solid phase to create a solid phase antigen; b) in a first assay, contacting a test sample from the patient with a liquid phase comprising no HCMV antigen and contacting a test sample from the patient with the coated solid phase of step a) for a time and under conditions sufficient for formation of antibody/antigen complexes; c) washing the coated solid phase of step b); d) in a second assay, contacting a test sample from the patient with the liquid phase antigen and contacting a test sample from the patient with the solid phase antigen for a time and under conditions sufficient for formation of antibody/antigen complexes; e) washing the contacted solid phase antigen of step d); f) adding a conjugate to the first and second assays for a time and under conditions sufficient for formation of anti-IgG/antibody/antigen complexes in the first and second assays, wherein the conjugate comprises an anti-IgG antibody attached to a signal-generating compound capable of generating a detectable signal; g) detecting a signal generated by the signal-generating compound in the first and second assays; and h) determining the ratio between the signal obtained in the second assay and the signal obtained in the first assay, wherein said ratio is proportional to the level of human anti-HCMV low avidity IgG antibody present in patient sample. The method may further comprise the step of: i) multiplying said ratio of step h) by 100 and subtracting the multiplied ratio from 100 in order to determine an Avidity Index, an Avidity Index of <50% indicating said patient has low avidity CMV IgG, an Avidity Index of ≧60% indicating said patient has high avidity CMV IgG, and an Avidity Index of 50% to 59% indicating the patient is equivocal for CMV IgG antibody avidity. Alternatively, the method may further comprise the step of: i) multiplying said ratio of step h) by 100 and subtracting the multiplied ratio from 100 in order to determine an Avidity Index, an Avidity Index of <40% indicating the patient has low avidity CMV IgG, an Avidity Index of ≧70% indicating the patient has high avidity CMV IgG, and an Avidity Index of 40% to 69% indicating the patient is equivocal for CMV IgG antibody avidity. (Again, an "equivocal" result is one that is uncertain and necessitates that another sample be taken from the patient (e.g., 2-3 weeks subsequent to the first test) and tested using the methods described herein. It is neither a low or high avidity IgG result. Further, an "equivocal" result may also be referred to as a "borderline", "grayzone", "mean" or "moderate" result.) A CMV low avidity IgG result indicates the patient has a primary CMV infection, and a CMV high avidity IgG result indicates the patient has a non-primary CMV infection.

The "at least one purified antigen" of the method may be, for example, pp38, pp53, pp65, p130 or pp150. (The purified or isolated antigen may be created by recombinant means, synthetic means or extracted from HMCV subsequent to transcription and translation of the proteins encoded by the organism's genome.) Further, the patient sample may be pretreated with solution prior to addition of the coated solid phase. Again, the solid phase may be, for example, a porous material, a non-porous material, a latex particle, a magnetic particle, a microparticle, a bead, a membrane, a microtiter well or a plastic tube.

All U.S. patents and publications referred to herein are hereby incorporated in their entirety by reference.

DETAILED DESCRIPTION OF THE INVENTION

Figure 1:
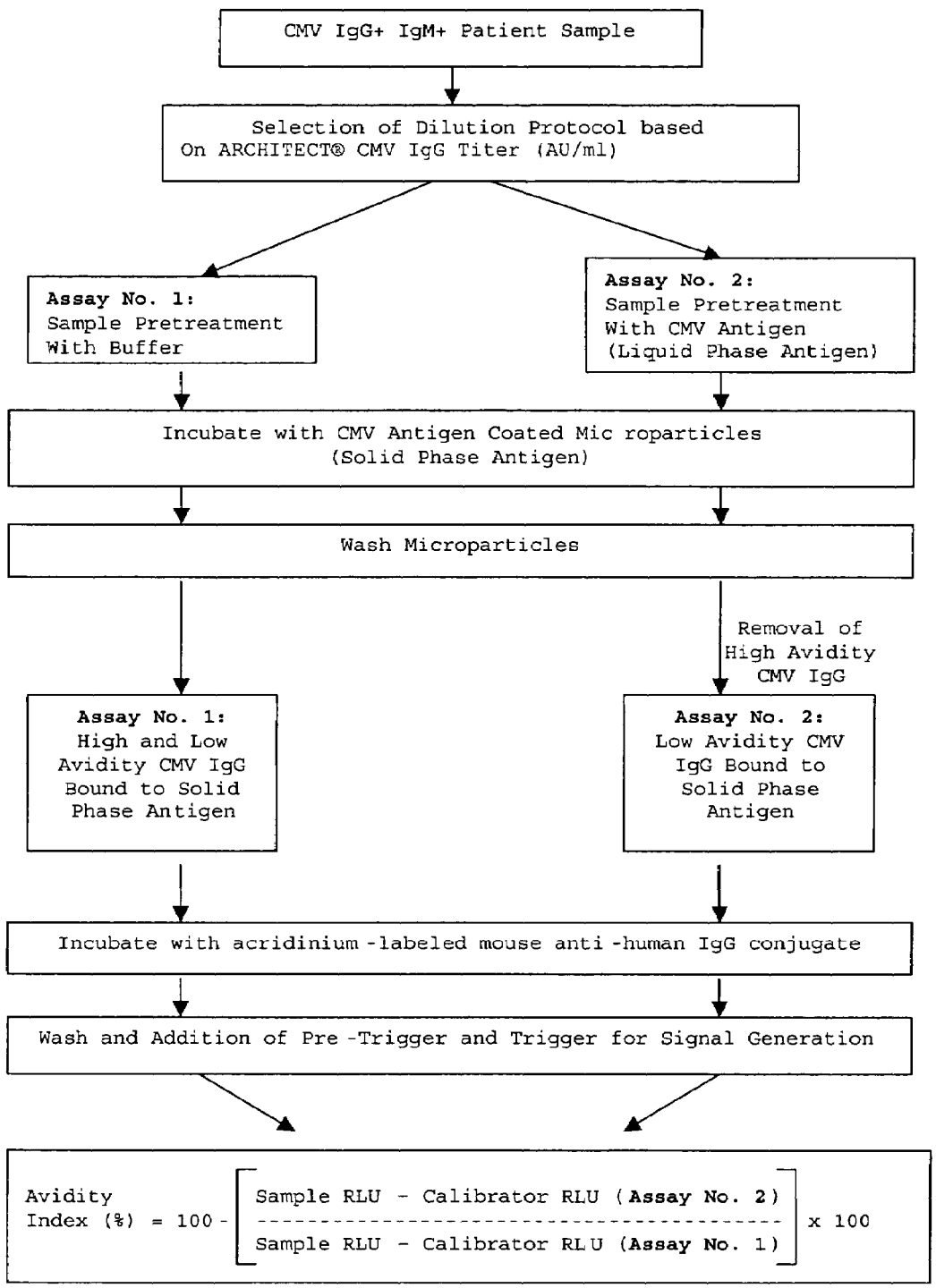
FIG. 1 is a schematic of the operation of Assay No. 1 and Assay No. 2 for the ARCHITECT® CMV IgG Avidity assay.

The difficulties of known assays using chaotropic agents for the determination of human anti-CMV and human anti-Toxo IgG antibody avidity have been described, in detail, above. In contrast, the methods of the present invention do not use chaotropic reagents. In particular, the methods of the present invention utilize the discovery that low avidity IgG antibodies produced during acute infection have a low affinity for "liquid phase antigen" and a high affinity for same "solid phase antigen". High avidity IgG antibodies produced during chronic infection, in contrast, have a preferential affinity for "liquid phase antigen" under optimal assay conditions, including optimal dilution of the patient sample. Thus, the methods of the present invention use the differential affinity of low and high avidity antibodies to "solid phase antigen" and same "liquid phase antigen" in order to distinguish between antibodies of low and high avidity and thereby discriminate at the diagnostic level between an acute infection and an infection acquired in the distant past (i.e., chronic infection, non-acute or non-primary infection). In terms of use, the avidity assays of the present invention may be used to aid in the diagnosis of CMV infection in pregnant women, for example, or to aid in the diagnosis of toxoplasmosis in pregnant women.

For purposes of the present invention, "antibody avidity" is defined as the sum of the binding affinities of the two Fab domains present on each IgG molecule and the antigen to which it binds.

A "liquid phase antigen" is defined as an antigen in solution, which comprises one or more epitopes that bind to an antibody also freely mobile within a solution. In contrast, a "solid phase antigen" is defined as an antigen that is attached to a solid phase, which comprises one or more epitopes that can capture an antibody in solution.

A "solid phase" may be a porous or non-porous material, a latex particle, a magnetic particle, a microparticle (see U.S. Pat. No. 5,705,330), a bead, a membrane, and a microtiter well or a plastic tube. The choice of solid phase material as well as method of labeling the antigen, if desired, is determined based upon desired assay format performance characteristics.

"Low avidity antibodies" are defined as those antibodies that are produced between 0 and 4 months post-infection. "High avidity antibodies" are defined as those antibodies that are produced greater than 4 months post-infection. During the course of infection, the overall avidity of the IgG antibodies produced in response to infection increases with time.

The "Avidity Index" for an avidity assay is defined as the proportion of high avidity IgG antibodies present in the patient sample times 100.

Examples of biological fluids which may be tested using the method of the present invention include whole blood, plasma, serum, cerebrospinal fluid, saliva, tears, nasal washes or aqueous extracts of tissues and cells.

An "infectious agent" is defined as an organism (e.g., bacteria, fungus, virus or parasite) that is capable of producing disease in a susceptible host.

The "conjugate" or "indicator reagent" will comprise an antibody or anti-antibody, attached to a "signal-generating compound" or "label". This "signal-generating compound" or "label" is in itself detectable or may be reacted with one or more additional compounds to generate a detectable product (see e.g., U.S. Pat. No. 6,395,472 B1). Examples of signal-generating compounds include chromogens, radioisotopes (e.g., 125I, 131I, 32P, 3H, 35 S and 14C), fluorescent compounds (e.g., fluorescein or rhodamine), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro- or lumo-genic substrate results in generation of a detectable signal. Other detection systems such as time-resolved fluorescence, internal-reflection fluorescence, amplification (e.g., polymerase chain reaction) and Raman spectroscopy are also useful.

The "solution" of the present invention is defined as an aqueous liquid between 0° C. and 37° C. Examples include buffers and diluents.

As noted above, one method of the present invention is a competitive antigen format for the determination of human anti-HCMV IgG antibody avidity. First, a HCMV antigen must be prepared that is capable of binding human anti-HCMV IgG antibodies in solution and when coated onto a solid phase. This viral antigen can be prepared by infection of mammalian cells in tissue culture with HCMV obtained from a clinical isolate or from a commercial stock of HCMV strain AD169, Towne, or Toledo (Trincado, D. E. et al. (2000) J. Med. Virol. 61, 481-487; Chee, M. S. et al. (1990) Curr. Top. Microbiol. Immunol. 154, 125-169; Lehner, R. et al. (1991) J. Clin. Microbiol. 29, 2494-2502) followed by purification of the virus from the infected cells. Alternatively, purified recombinant HCMV antigens can be prepared that are capable of binding human anti-HCMV IgG antibodies in solution and when coated onto a solid phase. These recombinant HCMV antigens can include but are not limited to pp38 (UL80a), pp52 (UL44), pp65 (UL83), p130 (UL57), pp150 (UL32) (Maine et al. (2001) Expert Rev. Molec. Diagn. 1, 19-29; U.S. Pat. No. 6,074,817).

The purified HCMV viral lysate, synthetic or recombinant antigens are then diluted into a solution (e.g., buffered antigen diluent)("liquid phase antigen") and also coated onto a solid phase ("solid phase antigen"). Two assays are then performed in the competitive antigen avidity assay format in order to determine the Avidity Index. In ASSAY No. 1 of the present invention (no HCMV soluble antigen), the patient sample is diluted with sample solution (e.g., diluent) and incubated with buffered antigen solution (e.g., diluent) containing no HCMV antigen and with the HCMV antigen coated solid phase. Alternatively, the diluted sample can be "pretreated" with the solution (e.g., buffered antigen diluent) containing no HCMV antigen prior to addition of the HCMV antigen coated solid phase. In this assay, both low and high avidity human anti-HCMV IgG antibodies bind to the "solid phase antigen". In parallel, in ASSAY No. 2 of the present invention (soluble HCMV antigen), the patient sample is diluted with sample solution (e.g., diluent) and incubated with buffered antigen solution (e.g., diluent) containing the HCMV antigen and with the HCMV antigen coated solid phase. Alternatively, the diluted sample can be "pretreated" with the buffered antigen solution containing the HCMV antigen prior to addition of the HCMV antigen coated solid phase. In this assay, low avidity human anti-HCMV IgG antibodies bind to the "solid phase antigen" whereas high avidity human anti-HCMV IgG antibodies bind to the "liquid phase antigen". After incubation of the patient sample with the buffered antigen solution (with or without soluble HCMV antigen) and HCMV antigen coated solid phase, a wash step is performed to remove human IgG antibodies not bound to the solid phase HCMV antigen. In ASSAY No. 1, only human IgG antibodies not specific for HCMV are removed. In ASSAY No. 2, the wash step removes human IgG antibodies not specific for HCMV and human anti-HCMV IgG high avidity antibodies bound to the "liquid phase antigen". Subsequently in both assays, an anti-human IgG conjugate containing a signal-generating compound is added and the signal obtained is proportional to the amount of human anti-HCMV IgG bound to the solid phase. Since the wash step following primary antibody incubation removes high avidity human anti-HCMV IgG, the ratio of the signal obtained in ASSAY No. 2 over the signal in ASSAY No. 1 is proportional to the level of human anti-HCMV low avidity IgG present in the sample. This is in contrast to the chaotropic avidity assay format, where the ratio of the signals obtained is proportional to the level of human anti-HCMV high avidity IgG present in the sample. This is due to the fact that the chaotropic avidity assay wash step removes IgG antibodies of low avidity, whereas the competitive antigen format of the present invention removes IgG antibodies of high avidity. Since the "Avidity Index" for an avidity assay is defined as the proportion of high avidity IgG antibodies present in the patient sample times 100, the results of the competitive antigen avidity assay are transformed mathematically as follows:

$$\text{Avidity Index } (\%) = 100 - \left[\frac{\text{Signal ASSAY No. 2}}{\text{Signal ASSAY No. 1}}\right] \times 100$$

Further, as noted above, another method of the present invention is a competitive antigen format for the determination of human anti-Toxo IgG antibody avidity. First, a *T. gondii* antigen must be prepared that is capable of binding human anti-Toxoplasma IgG antibodies in solution and when coated onto a solid phase. This parasite antigen can be prepared by infection of mice or mammalian cells in tissue culture with *T. gondii* obtained from a clinical isolate or from a commercial stock of strain RH, BK or C-56 (Reiter-Owona et al. (1999) Bull. World Health Org. 77, 929-935) followed by purification of the parasite antigen from mice or infected cells. Alternatively, purified recombinant *T. gondii* antigens can be prepared that are capable of binding human anti-Toxo IgG antibodies in solution and when coated onto a solid phase. These recombinant *T. gondii* antigens can include but are not limited to P22 (SAG2), P24 (GRA1), P25, P28 (GRA2), P29 (GRA7), P30 (SAG1), P35 (GRA8), P41 (GRA4), P54 (ROP2), P66 (ROP1), P68 (Prince et al. (1990) Mol. Biochem. Parasitol 43, 97-106; Cesbron-Delauw et al. (1989) Proc. Nat. Acad. Sci. 86, 7537-7541; Johnson et al. (1991) Gene 99, 127-132; Prince et al. (1989) Mol. Biochem. Parasitol. 34, 3-13; Bonhomme et al. (1998) J. Histochem. Cytochem. 46, 1411-1421; Burg et al. (1988) J. Immunol. 141, 3584-3591; Knapp et al. (1989) EPA 431541A2; Carey et al. (2000) Molec. Biochem. Parasitol. 105, 25-37; Mevelec et al. (1992) Mol. Biochem. Parasitol. 56, 227-238; Saavedra et al. (1991) J. Immunol. 147, 1975-1982); EPA 751 147).

The purified parasite, synthetic or recombinant *T. gondii* antigens are then diluted into a solution (e.g., buffered antigen diluent) ("liquid phase antigen") and also coated onto a solid phase ("solid phase antigen"). Two assays are then performed in the competitive antigen avidity assay format in order to determine the Avidity Index. In ASSAY No. 1 (no *T. gondii* soluble antigen), the patient sample is diluted with sample solution (e.g., diluent) and incubated with buffered antigen solution (e.g., diluent) containing no *T. gondii* antigen and with the *T. gondii* antigen coated solid phase. Alternatively, the diluted sample can be "pretreated" with the buffered antigen diluent containing no *T. gondii* antigen prior to addition of the *T. gondii* antigen coated solid phase. In this assay, both low and high avidity human anti-Toxo IgG antibodies bind to the "solid phase antigen". In parallel, in ASSAY No. 2 (soluble *T. gondii* antigen) the patient sample is diluted with sample solution (e.g., diluent) and incubated with buffered antigen solution (e.g., diluent) containing the *T. gondii* antigen and with the *T. gondii* antigen coated solid phase. Alternatively, the diluted sample can be "pretreated" with the buffered antigen solution (e.g., diluent) containing the *T. gondii* antigen prior to addition of the *T. gondii* antigen coated solid phase. In this assay, low avidity human anti-Toxo IgG antibodies bind to the "solid phase antigen" whereas high avidity human anti-Toxo IgG antibodies bind to the "liquid phase antigen". After incubation of the patient sample with the buffered antigen solution (with or without soluble *T. gondii* antigen) and *T. gondii* antigen coated solid phase, a wash step is performed to remove human IgG antibodies not bound to the solid phase *T. gondii* antigen. In ASSAY No. 1 only human IgG antibodies not specific for *T. gondii* are removed. In ASSAY No. 2, the wash step removes human IgG antibodies not specific for *T. gondii* and human anti-Toxo IgG high avidity antibodies bound to the "liquid phase antigen". Subsequently in both assays, an anti-human IgG conjugate containing a signal-generating compound is added, and the signal obtained is proportional to the amount of human anti-Toxo IgG bound to the solid phase. Since the wash step following primary antibody incubation removes high avidity human anti-Toxo IgG, the ratio of the signal obtained in ASSAY No. 2 over the signal in ASSAY No. 1 is proportional to the level of human anti-Toxo low avidity IgG present in the sample. This is in contrast to the chaotropic avidity assay format, where the ratio of the signals obtained is proportional to the level of human anti-Toxo high avidity IgG present in the sample. This is due to the fact that the chaotropic avidity assay wash step removes IgG antibodies of low avidity whereas the competitive antigen format of the present invention removes IgG antibodies of high avidity. Since the "Avidity Index" for an avidity assay is defined as the proportion of high avidity IgG antibodies present in the patient sample times 100, the results of the competitive antigen avidity assay are transformed mathematically as follows:

$$\text{Avidity Index } (\%) = 100 - \left[\frac{\text{Signal ASSAY No. 2}}{\text{Signal ASSAY No. 1}}\right] \times 100$$

As noted above, low avidity IgG antibodies produced during primary CMV infection or during acute toxoplasmosis have a low binding affinity for "liquid phase antigen" but a high binding affinity for "solid phase antigen" (e.g., antigen-coated microparticles or microtiter plates). In contrast, high avidity IgG antibodies produced during non-primary CMV infection or during a chronic toxoplasmosis preferentially bind "liquid phase antigen" and not "solid phase antigen" provided the "liquid phase antigen" is present in sufficient amounts to bind all high avidity anti-CMV or anti-Toxo IgG antibodies present in the patient sample of interest. This condition is met by diluting the patient sample as needed in the assay.

In order to ensure that the CMV and Toxo IgG avidity assays in the competitive antigen format described above perform as intended, assay-specific controls for CMV and Toxo, containing high and low avidity IgG, are run periodically to assess avidity assay validity. In order to manufacture these controls, source plasma must be obtained for control manufacture. High avidity IgG source plasma for CMV and Toxo is readily obtainable due to the seroprevalence for these diseases in the general population, i.e., healthy CMV or Toxo immune individuals can donate plasma containing high avidity IgG that can be used to manufacture high avidity IgG controls. In contrast, individuals in the acute phase of a CMV or Toxo infection, whose plasma contains low avidity IgG, may not be healthy and unable to donate their plasma for the manufacture of low avidity IgG controls. Furthermore, the acute phase of infection is relatively short and the incidence of infection for CMV and Toxo is relatively low, making it extremely difficult to source adequate amounts of low avidity IgG plasma for CMV and Toxo that are necessary for the manufacture of these important assay validity controls. Since the CMV and Toxo avidity assays described above require the proper dilution of patient samples to provide valid assay results, a high avidity IgG control, containing high-titer high avidity IgG, can "mimic" a low avidity control when run in a dilution protocol that does not dilute the control into the correct dilution range. Hence, another aspect of this invention is the development of "simulated" low avidity IgG controls for CMV and Toxo, wherein the IgG titer of said controls when run in the alternate protocol dilution for the low avidity control, overcomes the "blocking" by the "liquid phase antigen" resulting in a low avidity IgG result.

The present invention may be illustrated by use of the following non-limiting examples:

EXAMPLE 1

General Methodology

Materials and Sources

Tris-(hydroxymethyl)-aminomethane (TRIS), TRIS-HCL, sodium chloride, EDTA, sucrose, Quinolone (A56620), Nipasept (Sodium alkyl paraben), ProClin 300, ProClin 950, Bovine Serum Albumin (BSA), sodium hydroxide, hydrochloric acid, CAPS, CHAPS, azide, 2-(N-moropholino) ethanesulfonic acid (MES), sodium dodecyl sulfate (SDS), paramagnetic polystyrene microparticles, CMV antigen pool, Antifoam, Triton X-405, Triton X-100, Phenylmethylsulfonylchloride (PMSF), Lysozyme, Benzonase, magnesium chloride, maltose, Bovine Albumin Fraction V, Calf serum, Polysorbate 20, Sarafloxacin hydrochloride, Tween 20, Carnation non-fat dry milk, mouse immunoglobulin IgG, CKS antigen ammonium precipitated, 1-ethyl-3-(3-dimethylaminopropyl) carbodiimide (EDAC), CMV IgG positive high avidity recalcified human plasma, Toxo IgG positive high avidity recalcified human plasma, CMV IgG positive low avidity recalcified human plasma, CMV IgG negative recalcified human plasma, lamb serum, yeast extract, tryptone, glycerin, monobasic potassium phosphate, dibasic potassium phosphate, ampicillin, Defoamer Mazu DF-60, ammonium hydroxide, casamino acids, 6 N sulfuric acid, 6 N hydrochloric acid, 6 N sodium hydroxide, 0.5 M EDTA solution, pH 9, isopropyl-β-D-thiogalactoside (IPTG), phosphate buffered saline (PBS), Diethylaminoethyl (DEAE) Sepharose Fast Flow slurry, Amylose slurry, ARCHITECT® anti-human IgG acridinium-labeled conjugate concentrate, ARCHITECT® instrument, ARCHITECT® Line Diluent, Pre-Trigger Solution, Trigger Solution, and ARCHITECT® commodities were obtained from Abbott Manufacturing, Inc. (Abbott Park, Ill.). Radim CMV IgG avidity kits were purchased from Radim SpA (Rome, Italy). Vidas Toxo IgG avidity kits were purchased from BioMérieux SA (Lyon, France). Human anti-Toxoplasma P30 IgG monoclonal antibody was obtained from Celliance Corp. (Norcross, Ga.). The pMAL™ Protein Fusion and Purification System were purchased from New England Biolabs, Inc. (Beverly, Mass.). New England BioLabs' protocols were followed for the transformation of DNA into $E.$ $coli$ and for purification of maltose binding protein (MBP). EPICURIAN Coli™ XL-1 BLUE (recAl endAl gyrA96 thi-1 hsdR17 supE44 relA1 lac [F' proAB lacI$^q$ ZDM15 Tn10 (Tet$^r$)]) supercompetent $E.$ $coli$ cells were obtained from Stratagene Cloning Systems, Inc. (La Jolla, Calif.).

Media, Buffers and General Reagents

"ARCHITECT® CMV IgG Avidity Microparticle Diluent" and "ARCHITECT® CMV IgG Avidity Pretreatment 1 Buffer" contained 4.44 g/L TRIS, 2.65 g/L TRIS-HCL, 5 g/L sodium chloride, 3 g/L EDTA, 100 g/L sucrose, 0.01 g/L Quinolone (A56620), 1 g/L Nipasept (Sodium alkyl paraben), 1 g/L ProClin 300, 10 g/L BSA, adjusted pH to 8.4 with sodium hydroxide or hydrochloric acid. "ARCHITECT® CMV IgG Avidity Microparticle Coating Buffer" contained 22.14 g/L CAPS, 4.38 g/L sodium chloride, 1 g/L CHAPS, 1 g/L azide, adjusted pH to 11.0 with sodium hydroxide or hydrochloric acid. "ARCHITECT® CMV IgG Avidity Microparticle Concentrate Buffer" contained 2 L "ARCHITECT® CMV IgG Avidity Microparticle Coating Buffer", 3 L 50 mM MES buffer, pH 6.2, 0.2 L CMV antigen coated microparticles, and 1 L "ARCHITECT® CMV IgG Avidity Assay Microparticle Diluent". "ARCHITECT® CMV IgG Avidity Microparticle Bulk" contained 0.1 L "ARCHITECT® CMV IgG Microparticle Concentrate", 0.9 L "ARCHITECT® CMV IgG Avidity Microparticle Diluent", and 0.1 mL Antifoam. "ARCHITECT® CMV IgG Avidity Conjugate Diluent" contained 9.8 g/L MES, 29 g/L sodium chloride, 20 g/L BSA, 30 ml/L Triton X-405, 10 ml/L Quinolone (A56620), 1 g/L Nipasept (Sodium alkyl paraben), adjusted pH to 6.6 with sodium hydroxide or hydrochloric acid. "ARCHITECT® CMV IgG Avidity Conjugate Bulk" contained 0.03-0.06 mg/L ARCHITECT® anti-human IgG conjugate concentrate, 0.05 ml/L Antifoam, in "ARCHITECT® CMV IgG Avidity Conjugate Diluent". "ARCHITECT® CMV IgG Avidity Pretreatment 2 Blocker" contained 4.44 g/L TRIS, 2.65 g/L TRIS-HCL, 5 g/L sodium chloride, 3 g/L EDTA, 100 g/L sucrose, 0.01 g/L Quinolone (A56620), 1 g/L Nipasept (Sodium alkyl paraben), 1 g/L ProClin 300, 10 g/L BSA, 33.3-100 ml/L CMV antigen pool, adjusted pH to 8.4 with sodium hydroxide or hydrochloric acid. "ARCHITECT® CMV IgG High Avidity Control" contained CMV IgG positive high avidity recalcified plasma (Avidity Index range =70-100%), CMV IgG negative recalcified plasma, 1 g/L azide, and 15 ml/L 9.5% ProClin 950. "ARCHITECT® CMV IgG Low Avidity Control" contained CMV IgG positive low avidity recalcified plasma (Avidity Index range =10-30%), CMV IgG negative recalcified plasma, 1 g/L azide, and 15 ml/L 9.5% ProClin 950. "ARCHITECT® CMV IgG Avidity Background Calibrator" contained 0.25 L/L CMV IgG negative recalcified plasma, 0.75 L/L lamb serum, 15 ml/L 9.5% ProClin 950, and 1 g/L azide.

"MBP Inoculum Media" contained 24 g/L yeast extract, 12 g/L tryptone, 5 ml/L glycerin, 1.7 g/L Potassium phosphate monobasic, 11.4 g/L potassium phosphate dibasic, 0.05 g/L ampicillin. "MBP Fermentation Media" contained 24 g/L yeast extract, 12 g/L tryptone, 10 ml/L glycerin, 1.7 g/L potassium phosphate monobasic, 11.4 g/L potassium phosphate dibasic, 0.05 g/L ampicillin, 0.5 ml/L Defoamer, Mazu DF-60. "CKS Fermentation Media" contained 24 g/L yeast extract, 12 g/L tryptone, 15 ml/L glycerin, 1.7 g/L potassium phosphate monobasic, 11.4 g/L potassium phosphate dibasic, 10 g/L casamino acids, 0.05 g/L ampicillin, 0.5 ml/L Defoamer, Mazu DF-60. "MBP Lysis Buffer" contained 50 mM phosphate buffer, pH 7.5, 0.05% Triton X-100, 50 mM NaCl, and 1 mM EDTA.

"ARCHITECT® Toxo IgG Avidity Microparticle Diluent" contained 2.11 g/L TRIS, 11.43 g/L TRIS-HCL, 8 g/L sodium chloride, 3.72 g/L EDTA, 132.5 g/L sucrose, 0.005 g/L Quinolone (A56620), 1 g/L Nipasept (Sodium alkyl paraben), 18 ml/L Polysorbate 20, 102.5 g/L calf serum, adjusted pH to 7.5 with sodium hydroxide or hydrochloric acid. "ARCHITECT® Toxo IgG Avidity Pretreatment 1 Buffer" contained 2.13 g/L TRIS, 11.46 g/L TRIS-HCl, 9.87 g/L sodium chloride, 4.65 g/L EDTA, 0.005 g/L Quinolone, (A56620), 1 g/L Nipasept (Sodium alkyl paraben), 0.01% Antifoam, 0.1 g/L mouse IgG, adjusted pH to 7.5 with sodium hydroxide or hydrochloric acid. "ARCHITECT® Toxo IgG Avidity Pretreatment 2 Blocker" contained 2.13 g/L TRIS, 11.46 g/L TRIS-HCl, 9.87 g/L sodium chloride, 4.65 g/L EDTA, 0.005 g/L Quinolone, (A56620), 1 g/L Nipasept (Sodium alkyl paraben), 0.01% Antifoam, 0.1 g/L mouse IgG, 50-200 mg/L rpMBP-ToxoP30MIX1, adjusted pH to 7.5 with sodium hydroxide or hydrochloric acid. "ARCHITECT® Toxo IgG Avidity Microparticle Coating Buffer" contained 50 mM MES, 0.0005% Triton X-100, pH 6.2. "ARCHITECT® Toxo IgG Avidity Conjugate Diluent" contained 9.8 g/L MES, 29 g/L sodium chloride, 20 g/L Bovine Albumin Fraction V, 30 ml/L Triton X-405, 10 ml/L Quinolone (A56620), 1 g/L Nipasept (Sodium alkyl paraben), 0.8 g/L sodium azide, adjusted pH to 6.6 with sodium hydroxide or hydrochloric acid. "ARCHITECT® Toxo IgG Avidity Conjugate Bulk" contained 0.015-0.09 mg/L ARCHITECT® anti-human IgG conjugate concentrate, 1 ml/L Antifoam, in "ARCHITECT® Toxo IgG Avidity Conjugate Diluent". "ARCHITECT® Toxo IgG Avidity Assay Specific Diluent" contained 2.13 g/L TRIS, 11.43 TRIS-HCl g/L, 9.87 g/L sodium chloride, 300 ml/L calf serum, 4.65 g/L EDTA, 1 g/L Nipasept (Sodium alkyl paraben), 0.005 g/L Sarafloxacin Hydrochloride, 1.8 ml/L Tween 20, 10 g/L Carnation Non-Fat Dry Milk, 100 mg/L MBP lysate, 100 mg/L rpCKS ammonium sulfate precipitated, 100 mg/L mouse IgG, 1 ml/L Antifoam, adjusted pH to 7.5 with sodium hydroxide or hydrochloric acid. "ARCHITECT® Toxo IgG High Avidity Control" contained Toxo IgG positive high avidity recalcified plasma (Avidity Index range =60-100%), Toxo IgG negative recalcified plasma, 1 g/L azide, and 15 ml/L 9.5% ProClin 950. "ARCHITECT® Toxo IgG Low Avidity Control" contained human anti-Toxo P30 IgG low avidity monoclonal antibody (Avidity Index range=10-20%), BSA 10 g/L, 1 g/L azide, and 15 ml/L 9.5% ProClin 950. "ARCHITECT® CMV IgG Avidity Background Calibrator" contained ARCHITECT® Line Diluent.

EXAMPLE 2

Manufacture of the ARCHITECT® CMV IgG Avidity Assay Reagent Kit, Calibrator, Controls, and Assay Software Step A: Coating of CMV Viral Antigen Onto Microparticles and Manufacture of Microparticle Bulk Reagent Paramagnetic polystyrene microparticles were washed once with "ARCHITECT® CMV IgG Avidity Microparticle Coating Buffer" and then resuspended to a final concentration of 1% in coating buffer. The CMV antigen pool was thawed at room temperature, sonicated with 6×5 second bursts with pause amplitude of 30%, and then centrifuged at 500×g for 30 minutes to separate the virus from residual cell debris. The viral antigen supernatant,was added to the coating buffer containing microparticles at a concentration of approximately 1-25 ml viral antigen supernatant per liter of coating buffer and incubated for 30 minutes with stirring. The viral antigen coated microparticles were washed three times with 50 mM MES buffer, pH 6.2, and resuspended to a final concentration of 1% solids in "ARCHITECT® CMV IgG Avidity Microparticle Concentrate Buffer" and stored at 2 -8° C. The microparticle concentrate was then diluted 1:10 with "ARCHITECT® CMV IgG Avidity Microparticle Diluent", antifoam was added and the "ARCHITECT® CMV IgG Avidity Microparticle Bulk" reagent was filled into reagent bottles and stored at 2-8° C.

Step B: Manufacture of Conjugate Bulk Reagent

ARCHITECT® anti-human IgG acridinium-labeled conjugate was diluted to a final concentration of 30-60 ng/ml in "ARCHITECT® CMV IgG Avidity Conjugate Diluent" to yield the "ARCHITECT® CMV IgG Avidity Conjugate Bulk" which was then filled into reagent bottles and stored at 2-8° C.

Step C: Manufacture of Pretreatment 1 Buffer

"ARCHITECT® CMV IgG Avidity Pretreatment 1 Buffer" was prepared using the recipe in Example 1, which was then filled into reagent bottles and stored at 2-8° C.

Step D: Manufacture of Pretreatment 2 Blocker

"ARCHITECT® CMV IgG Avidity Pretreatment 2 Blocker" was prepared using the recipe in Example 1, which was then filled into reagent bottles and stored at 2-8° C. The "ARCHITECT® CMV IgG Reagent Pack" is defined as the reagents described in Examples 2A-2D.

Step E: Manufacture of Background Calibrator

"ARCHITECT® CMV IgG Avidity Background Calibrator" was prepared using the recipe in Example 1, which was then filled into reagent bottles and stored at 2 -8° C.

Step F: Manufacture of Controls

"ARCHITECT® CMV IgG High Avidity Control" and "ARCHITECT® CMV IgG Low Avidity Control" were prepared using the recipes in Example 1, which were then filled into reagent bottles and stored at 2-8° C.

Step G: Manufacture of Assay Software

The assay software required to run the ARCHITECT® CMV IgG Avidity assay on the ARCHITECT® instrument is provided on a CD-ROM to be loaded on the ARCHITECT® instrument prior to running the assay. The assay software controls the pipetting, dispensing, and mixing steps of all the reagents in the required sequence on the instrument in order to perform the assay as described below and as shown in FIG. 1.

EXAMPLE 3

Operation of the ARCHITECT® CMV IgG Avidity Assay

Step A: Configuration of the ARCHITECTS Instrument and Loading of the Reagent Pack The operator configures the ARCHITECT® instrument to perform the assay by loading the assay software from the CD-ROM (Abbott Laboratories, Abbott Park, Ill.). The software required to perform the assay contains two assay files, ASSAY no. 1 and ASSAY no. 2. ASSAY No. 1 and ASSAY No. 2 must be performed on each sample in order to calculate the Avidity Index as shown below. The operator also configures an additional assay file using the ARCHITECT® instrument user interface, which calculates the Avidity Index, according to the following formula:

$$\text{Avidity Index (\%)} = 100 - \left[ \frac{\text{Sample } RLU - \text{Calibrator } RLU \text{ (Assay No. 2)}}{\text{Sample } RLU - \text{Calibrator } RLU \text{ (Assay No. 1)}} \right] \times 100$$

"Sample RLU" is defined as the assay result of the patient sample expressed in Relative Light Units (RLU); "Calibrator RLU" is defined as the assay result in RLU using the "ARCHITECT® CMV IgG Avidity Background Calibrator"; "ASSAY No. 2" is defined as the assay which pretreats the sample, control, or calibrator with the "ARCHITECT® CMV IgG Avidity Pretreatment 2 Blocker"; "ASSAY No. 1" is defined as the assay which pretreats the sample, control, or calibrator with the "ARCHITECT® CMV IgG Avidity Pretreatment 1 Buffer"; and the "Avidity Index" is defined by the equation above and expressed in percent is proportional to the level of human anti-HCMV high avidity IgG present in the sample. Samples which have an Avidity Index value of <50% contain low avidity CMV IgG, ≧60% contain high avidity CMV IgG, and between 50 to 59% are equivocal for CMV IgG antibody avidity.

The operator loads the "ARCHITECT® CMV IgG Reagent Pack" on the ARCHITECT® instrument as follows: "ARCHITECT® CMV IgG Avidity Pretreatment 1 Buffer" is loaded into Position No. 1, color coded yellow; "ARCHITECT® CMV IgG Avidity Microparticle Bulk" is loaded into Position No. 2, color coded pink; "ARCHITECT® CMV IgG Avidity Conjugate Bulk" is loaded into Position No. 3, color coded black; and "ARCHITECT® CMV IgG Avidity Pretreatment 2 Blocker" is loaded into Position No. 5, color coded pink.

Step B: Ordering the ARCHITECT® CMV IgG Avidity Test

Prior to running the ARCHITECT® CMV IgG avidity test, the operator must select the appropriate dilution protocol for ASSAY Nos. 1 and 2 based on the CMV IgG titer of each sample expressed in AU/ml from the ARCHITECT® CMV IgG assay as follows: Dilution Protocol No. 1, 5-16 AU/ml; Dilution Protocol No. 2, 16-50 AU/ml; Dilution Protocol No. 3, 50-150 AU/ml; Dilution Protocol No. 4, 150-500 AU/ml; for samples with a CMV IgG titer >500 AU/ml, the sample is manually diluted to a titer of 10 AU/ml and Dilution Protocol No. 1 is run. The samples are then loaded onto to the instrument. The "ARCHITECT® CMV IgG Avidity Background Calibrator" is loaded onto to the instrument for calibration of the assay and the "ARCHITECT® CMV IgG High Avidity Control" and "ARCHITECT® CMV IgG Low Avidity Control" is loaded to ensure the assay results are valid.

Step C: Description of the ARCHITECT® CMV IgG Avidity Assay

Approximately 10-72 µl of each sample is needed for ASSAY Nos. 1 and 2 depending on the dilution protocol requested by the operator. The following steps for ASSAY Nos. 1 and 2 are identical except for the pretreatment step: The pipetting probe aspirates the amount of sample required for each assay and performs the appropriate sample dilution with ARCHITECT® Line Diluent; in the pretreatment step for ASSAY No. 2, the pipetting probe dispenses "ARCHITECT® CMV IgG Avidity Pretreatment 2 Blocker", which contains the HCMV viral ant igen present in the liquid phase and which binds human anti -HCMV high avidity IgG, into the diluted sample; in the pretreatment step for ASSAY No. 1, the pipetting probe dispenses "ARCHITECT® CMV IgG Avidity Pretreatment 1 Buffer", which contains buffer only, into the diluted sample; the pretreated samples incubate for 7 minutes; the pipetting probe then dispenses 50 µl of "ARCHITECT® CMV IgG Avidity Microparticle Bulk" into the "pretreated samples" and the samples are incubated for 18 minutes; human anti-HCMV IgG antibodies of low avidity bind to the solid phase coated HCMV viral antigen in ASSAY No. 2 whereas human anti-HCMV IgG antibodies of high and low avidity bind to the solid phase coated HCMV viral antigen in ASSAY No. 1; the microparticles are then washed with ARCHITECT® Line Diluent and then the pipetting probe dispenses 50 µl of the "ARCHITECT® CMV IgG Avidity Conjugate Bulk" and the microparticles are incubated with the conjugate for 4 minutes; the microparticles are washed again with ARCHITECT® Line Diluent and then treated with ARCHITECT® Pre-Trigger and Trigger reagent; the resulting chemiluminescence signal generated is read by the ARCHITECT® instrument and displayed as RLU for each sample and stored for ASSAY No. 1 and ASSAY No. 2; after the run is complete the instrument subtracts the "ARCHITECT® CMV IgG Avidity Background Calibrator" RLU from each sample for ASSAY No. 1 and ASSAY No. 2 and calculates the Avidity Index as described above; next to the Avidity Index result the interpretation of the result is also displayed according to the following algorithm; samples which have an Avidity Index value of <50% contain low avidity CMV IgG; ≧60% contain high avidity CMV IgG; and between 50 to 59% are equivocal for CMV IgG antibody avidity.

EXAMPLE 4

Evaluation of the ARCHITECT® CMV IgG Avidity Assay

Step A: Human Sera for Testing

Three groups of sera were tested in this evaluation: Group 1 (n=256) consisted of random blood donor sera (n=126) and pregnant women (n=130) that were negative for CMV IgM antibody and positive for CMV IgG antibody; Group 2 (n=35) consisted of serial bleeds from three individuals with primary HCMV infection as documented by seroconversion (n=2) or by the presence of CMV IgM antibodies and low avidity CMV IgG (n=1); Group 3 (n=37) consisted of serial bleeds from 20 pregnant women with primary HCMV infection as documented by seroconversion (n=18) or by the presence of CMV IgM antibodies and low avidity CMV IgG (n=2).

Step B: Comparison of the Performance of the ARCHITECT® CMV IgG Avidity Assay to the Radim CMV IgG Avidity Assay and Clinical Data The Radim CMV IgG avidity assay (Radim SpA, Rome, Italy) consists of two CMV IgG assays run in duplicate and distinguishes between specimens containing low and high avidity by incorporating a chaotropic wash step with urea after primary antibody incubation in one of the two CMV IgG assays. The Avidity Index for the Radim CMV IgG avidity assay (Radim SpA, Rome, Italy) was calculated as follows per the manufacturer's package insert using Optical Density (O.D.):

$$\text{Avidity Index } (\%) = \frac{O.D. \text{ with Dissoc. Reagent } (Urea)}{O.D. \text{ with Sample Diluent}} \times 100$$

Results for this assay were interpreted according to the Radim package insert (Radim SpA, Rome, Italy).

Samples from Group 1 (CMV IgM−IgG+) were used to assess the clinical specificity of the avidity assays. Samples that are negative for CMV IgM and positive for CMV IgG antibody should contain high avidity IgG as this population is immune to HCMV and does not have an active HCMV infection. The results with samples from Group 1 are shown below in Table 1:

TABLE 1

Evaluation of the ARCHITECT ® CMV IgG Avidity Assay on Samples from Group 1 (CMV IgG+ IgM−)

|  |  | Radim CMV IgG Avidity | | | |
|---|---|---|---|---|---|
|  |  | LOW | EQV | HIGH | TOTAL |
| ARCHITECT ® | LOW | 1 | 0 | 0 | 1 |
| CMV IgG | EQV | 0 | 0 | 4 | 4 |
| Avidity | HIGH | 1 | 0 | 250 | 251 |
|  | TOTAL | 2 | 0 | 254 | 256 |

ARCHITECT ®/Radim Relative Agreement: 251/252 = 99.6%
ARCHITECT ® Clinical Specificity: 251/252 = 99.6%
Radim Clinical Specificity: 254/256 = 99.2%
Radim (Radim SpA, Rome, Italy)

As can be seen from Table 1, the ARCHITECT® and Radim avidity assay (Radim SpA, Rome, Italy) sample results are in excellent agreement, i.e. samples with low and high avidity results in the ARCHITECT® assay also have corresponding low and high avidity results, respectively, in the Radim assay (Radim SpA, Rome, Italy). Both assays also demonstrate high clinical specificity, i.e. almost all samples that were negative for CMV IgM and positive for CMV IgG antibody contained high avidity CMV IgG.

Samples from Group 2 and Group 3 were used to assess the clinical sensitivity of the avidity assays. These samples were from individuals with primary HCMV infection. A cutoff of 4 months was chosen for the evaluation of clinical sensitivity and is based on the ability of an avidity assay to exclude a primary HCMV infection in pregnant women during the first trimester of gestation (3 months). The results with samples from Group 2 and Group 3 are shown in Table 2:

TABLE 2

Evaluation of the ARCHITECT® CMV IgG Avidity Assay on Samples from Group 2 and Group 3

|  |  | Radim CMV IgG Avidity | | | |
|---|---|---|---|---|---|
|  |  | LOW | EQV | HIGH | TOTAL |
| ARCHITECT® | LOW | 59 | 8 | 3 | 70 |
| CMV IgG | EQV | 0 | 0 | 0 | 0 |
| Avidity | HIGH | 0 | 1 | 1 | 2 |
|  | TOTAL | 59 | 9 | 4 | 72 |

ARCHITECT®/Radim Relative Agreement: 60/63 = 95.2%
ARCHITECT® Clinical Sensitivity: 70/72 = 97.2%
Radim Clinical Sensitivity: 59/63 = 93.7%
Radim (Radim SpA, Rome, Italy)

As can be seen from Table 2, the ARCHITECT® and Radim assays (Radim SpA, Rome, Italy) are in good agreement with one another, i.e. samples with low and high avidity results in the ARCHITECT® assay also have corresponding low and high avidity results, respectively, in the Radim assay (Radim SpA, Rome, Italy). Both assays also demonstrate good clinical sensitivity. The rate of maturation of avidity appears to be slower for the ARCHITECT® assay relative to the Radim assay (Radim SpA, Rome, Italy) as shown by the 11 samples that were low avidity by the ARCHITECT® assay and equivocal (n=8) or high (n=3) by the Radim assay (Radim SpA, Rome, Italy). Based on these data the ARCHITECT® CMV IgG avidity assay is more sensitive for the detection of primary HCMV infection.

The correlation between the ARCHITECT® and Radim CMV IgG avidity assay (Radim SpA, Rome, Italy) results was evaluated across samples from Groups 1-3 (n=215) and a correlation coefficient of r=0.88 was obtained. This was a surprising and unexpected result for two reasons: first, the avidity assays are qualitative and hence quantitative agreement would not necessarily be expected; and second, they use very different assay formats, i.e., the competitive antigen format selectively removes high avidity IgG from the patient sample whereas the chaotropic format removes low avidity IgG in a wash step.

There are several advantages of the competitive antigen format of the ARCHITECT® CMV IgG avidity of the present invention over the chaotropic format of other CMV IgG avidity assays. First, no chaotropic reagents are required to perform the assay. Chaotropic reagents can be hazardous or corrosive to an automated immunoassay instrument platform and may also cross-contaminate other assays thereby causing aberrant results. Second, it is known that the Avidity Index is affected to some extent by the anti-human IgG concentration against an infectious agent (Hedman, K. and Seppala, I., supra). Most conventional avidity assays employing chaotropic reagents do not compensate for this effect whereas the present invention utilizes a series of dilution protocols to dilute samples in the appropriate range, thus ensuring that the Avidity Index result is not confounded by the anti-IgG titer present in patient samples. Finally, the competitive antigen format of the present invention demonstrated better detection of specimens from patients with primary HCMV infection.

EXAMPLE 5

Manufacture of MBP Lysate and rpMBP-ToxoP30MIX1

The *E. coli* maltose binding protein (MBP) fusion and purification system described in U.S. Pat. No. 5,643,758 has been found to be useful for the production and purification of soluble fusion proteins in *E. coli*. The plasmid pMAL-c2X was obtained from New England BioLabs, Inc. and transformed into *E. coli* supercompetent cells EPICURIAN *Coli*™ XL-1 BLUE using supplier protocols. This strain was subsequently used for the production of MBP lysate. The EPICURIAN *Coli*™ XL-1 BLUE *E. coli* strain containing the pMBP-c2X-ToxoP30MIX1 construct described in U.S. Ser. 10/263,153 was used for the production of purified rpMBP-ToxoP30. The EPICURIAN *Coli*™ XL-1 BLUE *E. coli* strain containing the CKS-ToxoP35-CKS construct described in U.S. Pat. No. 6,329,157 B1 was used for the production of purified rpCKS-ToxoP35 protein.

Step A: Preparation of MBP Lysate

*E. coli* strain containing plasmid pMAL-c2X was inoculated into a flask with "MBP Inoculum Media" and grown at 37° C. with shaking to an O.D. at 600 nm of 0.8-1.2. This culture was used to inoculate a 10L fermentor containing "MBP Fermentation Media" and grown at 37° C., agitation at 500 rpm, aeration at 15 slpm, and pressure at 345 mbar. The fermentation culture was grown to an O.D. at 600 nm of 6.0-8.0 and then induced with 50 mg/L IPTG. After 4 hours post induction, the fermentor harvest was concentrated by diafiltration against PBS and centrifuged at 14,000×g for 25 minutes at 2-8° C. The fermentor cell paste was aliquoted and then stored at −70° C. until production of lysate.

The cell paste was thawed and transferred to 10 ml "MBP Lysis Buffer" per gram of cell paste containing 0.2 ml/L Benzonase solution, 6.2 g/L magnesium chloride, and 2 g/L Lysozyme and homogenized. PMSF solution was added (1 ml/g cell paste), homogenized, and incubated for 60 minutes at 37° C. with shaking. An equal volume of cold distilled water was then added and incubated for 15 minutes at 37° C. with shaking. The lysed cell paste was centrifuged at 15,000×g for 45 minutes at 2-8° C. The supernatant was recovered, clarified by filtration through a 0.2μ filter, and stored at −70° C.

Step B: Purification of rpMBP-ToxoP30MIX1

*E. coli* strain containing plasmid pMBP-c2X-ToxoP30MIX1 was inoculated into a flask with "MBP Inoculum Media" and grown at 36° C. with shaking to an O.D. at 600 nm of 0.8-1.2. This culture was used to inoculate a lOL fermentor containing "MBP Fermentation Media" and grown at 36° C., agitation at 500 rpm, aeration at 15 slpm, and pressure at 345 mbar. The fermentation culture was grown to an O.D. at 600 nm of 6.0-8.0 and then induced with 50 mg/L IPTG. After 4 hours post induction, the fermentor harvest was concentrated by diafiltration against PBS and centrifuged at 14,000×g for 25 minutes at 2-8° C. The fermentor cell paste was aliquoted and then stored at −70° C. until purification of the protein.

The cell paste was thawed and transferred to 10 ml "MBP Lysis Buffer" per gram of cell paste containing 0.2 ml/L Benzonase solution, 6.2 g/L magnesium chloride, and 2 g/L Lysozyme and homogenized. PMSF solution was added (1 ml/g cell paste), homogenized, and incubated for 60 minutes at 37° C. with shaking. An equal volume of cold distilled water was then added and incubated for 15 minutes at 37° C. with shaking. The lysed cell paste was centrifuged at 15,000×g for 45 minutes at 2-8° C. The supernatant was recovered and clarified by filtration through a 0.2μ filter.

The supernatant was then applied to a DEAE Sepharose Fast Flow column equilibrated with 50 mM phosphate buffer, pH 7.4, 25 mM NaCl, and 1 mM EDTA. The column was extensively washed with this buffer and then eluted with 50 mM phosphate buffer, pH 7.4, 200 mM NaCl, 1 mM EDTA and the eluted peak pool was stored for 12 to 24 hours at 2-8° C.

The peak pool protein fraction from the DEAE column was applied to an Amylose resin column equilibrated with 50 mM phosphate buffer, pH 7.4, 50 mM NaCl, 1 mM EDTA. The column was washed extensively with this buffer and the rpMBP-ToxoP30 protein was then eluted with 50 mM NaCl, 10 mM maltose, 0.2% azide. The eluted peak pool was recovered and clarified by filtration through a 0.2µ filter and stored at −70° C. until microparticle coating.

EXAMPLE 6

Manufacture of the ARCHITECT® Toxo IgG Avidity Assay Reagent Kit, Calibrator, Controls, and Assay Software Step A: Coating of rpMBP-ToxoP30 Antigen Onto Microparticles and Manufacture of Microparticle Bulk Reagent The rpMBP-ToxoP30MIX1 antigen was thawed at ambient temperature and diluted to a final concentration of 1 mg/ml in 50 mM phosphate, 50 mM sodium chloride, 1 mM EDTA, 10 mM maltose, 0.2% azide, pH 7.5 and incubated for 5 days at 37° C. to refold the antigen. The antigen was then stored at 2-8 ° C. for 1 day prior to coating microparticles.

Paramagnetic polystyrene microparticles were washed twice with "ARCHITECT® Toxo IgG Avidity Microparticle Coating Buffer" and then resuspended to a final concentration of 1.33% in coating buffer. The refolded rpMBP-ToxoP30MIX1 antigen was then added to the washed microparticles at a final protein concentration of 100 µg/ml and mixed for 10 minutes at 15-30° C. EDAC was then added to the microparticle coating reaction at a final concentration of 1 mg/ml and incubated with mixing for 30 minutes at 15-30° C. A 1 M TRIS buffer, pH 8.0 was added to the microparticle coating reaction to a final concentration of 0.1 M and incubated with mixing for an additional 30 minutes at 15-30° C. The coated microparticles were then washed with 50 mM MES, pH 6.2 to remove unbound antigen, reactants, and resuspended to a final concentration of 1% solids in "ARCHITECT® Toxo IgG Avidity Microparticle Diluent." The "ARCHITECT® Toxo IgG Avidity Microparticle Bulk Reagent" was prepared by diluting the microparticle concentrate to a final concentration of 0.1% solids with "ARCHITECT® Toxo IgG Avidity Microparticle Diluent", which was then filled into reagent bottles and stored at 2-8° C.

Step B: Manufacture of Conjugate Bulk Reagent

ARCHITECT® anti-human IgG acridinium-labeled conjugate was diluted to a final concentration of 15-90 ng/ml in "ARCHITECT® Toxo IgG Avidity Conjugate Diluent" to yield the "ARCHITECT® Toxo IgG Avidity Conjugate Bulk" which was then filled into reagent bottles and stored at 2 -8° C.

Step C: Manufacture of Pretreatment 1 Buffer

"ARCHITECT® Toxo IgG Avidity Pretreatment 1 Buffer" was prepared using the recipe in Example 1, which was then filled into reagent bottles and stored at 2-8° C.

Step D: Manufacture of Pretreatment 2 Blocker

"ARCHITECT® Toxo IgG Avidity Pretreatment 2 Blocker" was prepared using the recipe in Example 1, which was then filled into reagent bottles and stored at 2-8° C.

Step E: Manufacture of Assay Specific Diluent

"ARCHITECT® Toxo IgG Avidity Assay Specific Diluent" was prepared using the recipe in Example 1, which was then filled into reagent bottles and stored at 2-8° C. The "ARCHITECT® Toxo IgG Reagent Pack" is defined as the reagents described in Examples 6A-6E.

Step F: Manufacture of Background Calibrator

"ARCHITECT® Toxo IgG Avidity Background Calibrator" was prepared using the recipe in Example 1, which was then filled into reagent bottles and stored at 2-8° C.

Step G: Manufacture of Controls

"ARCHITECT® Toxo IgG High Avidity Control" and "ARCHITECT® Toxo IgG Low Avidity Control" were prepared using the recipes in Example 1, which were then filled into reagent bottles and stored at 2-8° C.

Step H: Manufacture of Assay Software

Figure 2:
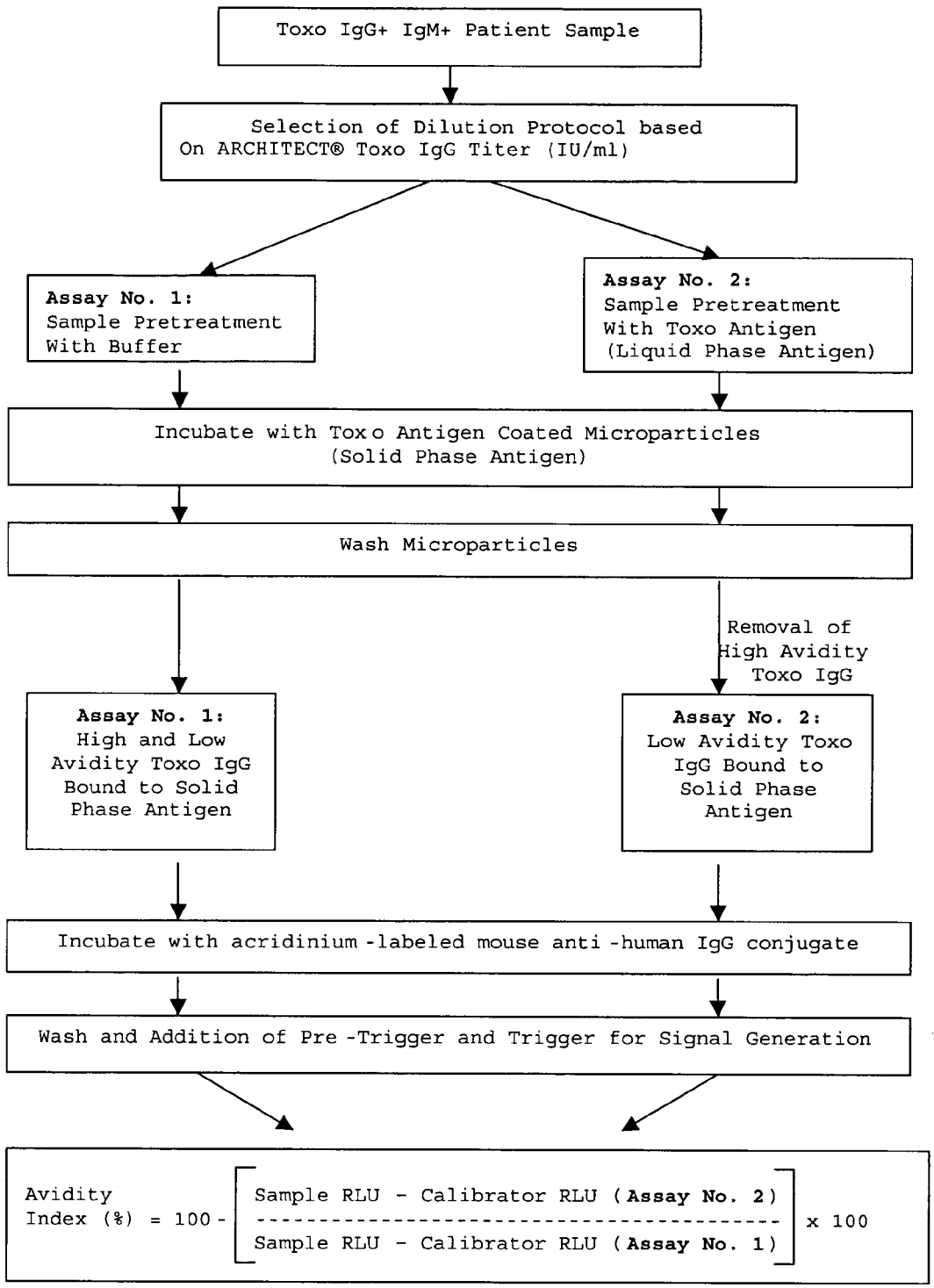
FIG. 2 is a schematic of the operation of Assay No. 1 and Assay No. 2 for the ARCHITECT® Toxo IgG Avidity assay.

The assay software required to run the ARCHITECT® Toxo IgG Avidity assay on the ARCHITECT® instrument is provided on a CD-ROM to be loaded on the ARCHITECT® instrument prior to running the assay (Abbott Laboratories, Abbott Park, Ill.). The assay software controls the pipetting, dispensing, and mixing steps of all the reagents in the required sequence on the instrument in order to perform the assay as described below and as shown in FIG. 2.

EXAMPLE 7

Operation of the ARCHITECT® Toxo IgG Avidity Assay

Step A: Configuration of the ARCHITECT® Instrument and Loading of the Reagent Pack The operator configures the ARCHITECT® instrument to perform the assay by loading the assay software from the CD-ROM. The software required to perform the assay contains two assay files, ASSAY no. 1 and ASSAY no. 2. ASSAY No. 1 and ASSAY No. 2 must be performed on each sample in order to calculate the Avidity Index as shown below. The operator also configures an additional assay file using the ARCHITECT® instrument user interface, which calculates the Avidity Index, according to the following formula:

$$\text{Avidity Index (\%)} = 100 - \left[ \frac{\text{Sample } RLU - \text{Calibrator } RLU \text{ (Assay No. 2)}}{\text{Sample } RLU - \text{Calibrator } RLU \text{ (Assay No. 1)}} \right] \times 100$$

"Sample RLU" is defined as the assay result of the patient sample expressed in Relative Light Units (RLU); "Calibrator RLU" is defined as the assay result in RLU using the "ARCHITECT® Toxo IgG Avidity Background Calibrator"; "ASSAY No. 2" is defined as the assay which pretreats the sample, control, or calibrator with the "ARCHITECT® Toxo IgG Avidity Pretreatment 2 Blocker"; "ASSAY No. 1" is defined as the assay which pretreats the sample, control, or calibrator with the "ARCHITECT® Toxo IgG Avidity Pretreatment 1 Buffer"; and the "Avidity Index" is defined by the equation above and expressed in percent is proportional to the level of human anti-Toxo high avidity IgG present in the sample. Samples which have an Avidity Index value of <30% contain low avidity Toxo IgG, ≧40% contain high avidity Toxo IgG, and between 30 to 39% are equivocal for Toxo IgG antibody avidity.

The operator loads the "ARCHITECT® Toxo IgG Reagent Pack" on the ARCHITECT® instrument as follows: "ARCHITECT® Toxo IgG Avidity Assay Specific Diluent" is loaded into Position No. 1, color coded yellow; "ARCHITECT® Toxo IgG Avidity Microparticle Bulk" is loaded into Position No. 2, color coded pink; "ARCHITECT® Toxo IgG Avidity Conjugate Bulk" is loaded into Position No. 3, color coded black; "ARCHITECT® Toxo IgG Avidity Pretreatment 1 Buffer" is loaded into Position No. 4, color coded yellow; and "ARCHITECT® Toxo IgG Avidity Pretreatment 2 Blocker" is loaded into Position No. 5, color coded pink.

Step B: Ordering the ARCHITECT® Toxo IgG Avidity Test

Prior to running the ARCHITECT® Toxo IgG avidity test, the operator must select the appropriate dilution protocol for ASSAY Nos. 1 and 2 based on the Toxo IgG titer of each sample expressed in IU/ml from the ARCHITECT® Toxo IgG assay as follows: Dilution Protocol No. 1, 3-20 IU/ml; Dilution Protocol No. 2, 21-200 IU/ml; Dilution Protocol No. 3, 201-2000 IU/ml; for samples with a Toxo IgG titer>2000 IU/ml, the sample is manually diluted to a titer of 10 IU/ml and Dilution Protocol No. 1 is run. The samples are then loaded onto to the instrument. The "ARCHITECT® Toxo IgG Avidity Background Calibrator" is loaded onto to the instrument for calibration of the assay and the "ARCHITECT® Toxo IgG High Avidity Control" and "ARCHITECT® Toxo IgG Low Avidity Control" is loaded to ensure the assay results are valid.

Step C: Description of the ARCHITECT® Toxo IgG Avidity Assay

Approximately 5-80 µl of each sample is needed for ASSAY Nos. 1 and 2 depending on the dilution protocol requested by the operator. The following steps for ASSAY Nos. 1 and 2 are identical except for the pretreatment step: The pipetting probe aspirates the amount of sample required for each assay and performs the appropriate sample dilution with ARCHITECT® Line Diluent; in the pretreatment step for ASSAY No. 2, the pipetting probe dispenses "ARCHITECT® Toxo IgG Avidity Pretreatment 2 Blocker", which contains the rpMBP-ToxoP30MIX1 antigen present in the liquid phase and which binds human anti-Toxo high avidity IgG, into the diluted sample; in the pretreatment step for ASSAY No. 1, the pipetting probe dispenses "ARCHITECT® Toxo IgG Avidity Pretreatment 1 Buffer", which contains buffer only, into the diluted sample; the pretreated samples incubate for 7 minutes; the pipetting probe then dispenses 90 µl "ARCHITECT® Toxo IgG Avidity Assay Specific Diluent" and 50 µl of "ARCHITECT® Toxo IgG Avidity Microparticle Bulk" into 23 µl of the pretreatment reaction and the samples are incubated for 18 minutes; human anti-Toxo IgG antibodies of low avidity bind to the solid phase coated rpMBP-ToxoP30MIX1 antigen in ASSAY no. 2 whereas human anti-Toxo IgG antibodies of high and low avidity bind to the solid phase coated rpMBP-ToxoP30MIX1 antigen in ASSAY no. 1; the microparticles are then washed with ARCHITECT® Line Diluent and then the pipetting probe dispenses 50 µl of the "ARCHITECT® Toxo IgG Avidity Conjugate Bulk" and the microparticles are incubated with the conjugate for 4 minutes; the microparticles are washed again with ARCHITECT® Line Diluent and then treated with ARCHITECT® Pre-Trigger and Trigger reagent; the resulting chemiluminescence signal generated is read by the ARCHITECT® instrument and displayed as RLU for each sample and stored for ASSAY No. 1 and ASSAY No. 2; after the run is complete the instrument subtracts the "ARCHITECT® Toxo IgG Avidity Background Calibrator" RLU from each sample for ASSAY No. 1 and ASSAY No. 2 and calculates the Avidity Index as described above; next to the Avidity Index result the interpretation of the result is also displayed according to the following algorithm; samples which have an Avidity Index value of <30% contain low avidity Toxo IgG; ≧40% contain high avidity Toxo IgG; and between 30 to 39% are equivocal for Toxo IgG antibody avidity.

EXAMPLE 8

Evaluation of the ARCHITECT® Toxo IgG Avidity Assay

Step A: Human Sera for Testing

Two groups of sera were tested in this evaluation: Group 1 (n=138) consisted of random individuals from France that were negative for Toxo IgM antibody and positive for Toxo IgG antibody; Group 2 (n=23) consisted of serial bleeds from two individuals with an acute toxoplasmosis as documented by seroconversion; Group 3 (n=24) consisted of selected individuals that were positive for Toxo IgG antibody.

Step B: Comparison of the Performance of the ARCHITECT® Toxo IgG Avidity Assay to the Vidas Toxo IgG Avidity Assay and Clinical Data The Vidas Toxo IgG avidity assay (BioMérieux SA, Lyon, France) consists of two Toxo IgG assays run in duplicate and distinguishes between specimens containing low and high avidity by incorporating a chaotropic wash step with urea after primary antibody incubation in one of the two Toxo IgG assays. The Avidity Index for the Vidas Toxo IgG avidity assay (BioMérieux SA, Lyon, France) was calculated as follows per the manufacturer's package insert using Relative Fluorescence Value (RFV):

$$\text{Avidity Index (\%)} = \frac{\text{Test } RFV \text{ with Dissoc. Reagent } (Urea)}{\text{Reference } RFV \text{ without Dissoc. Reagent}} \times 100$$

Results for this assay were interpreted according to the Vidas package insert (BioMérieux SA, Lyon, France).

Samples from Group 1 (Toxo IgM−IgG+) were used to assess the clinical specificity of the ARCHITECT® Toxo IgG avidity assay. Samples that are negative for Toxo IgM and positive for Toxo IgG antibody should contain high avidity IgG as this population is immune to *T. gondii* and does not have an active *T. gondii* infection. The results with samples from Group 1 are shown below in Table 3:

TABLE 3

Evaluation of the ARCHITECT ® Toxo IgG Avidity Assay on Samples from Group 1 (Toxo IgG+ IgM−)

| ARCHITECT ® Toxo IgG Avidity | | | |
|---|---|---|---|
| LOW | EQV | HIGH | TOTAL |
| 1 | 1 | 136 | 138 |

ARCHITECT ® Clinical Specificity: 136/137 = 99.3%

As can be seen from Table 3, the ARCHITECT® Toxo IgG avidity assay demonstrates high clinical specificity, i.e., almost all samples that were negative for Toxo IgM and positive for Toxo IgG antibody contained high avidity Toxo IgG.

Samples from Group 2 and Group 3 were used to assess the agreement and correlation between the ARCHITECT® Toxo IgG and Vidas Toxo IgG avidity assays (BioMérieux SA, Lyon, France). These samples were from individuals with acute toxoplasmosis as documented by seroconversion and from selected Toxo IgG positive individuals. The results with samples from Group 2 and Group 3 are shown in Table 4:

TABLE 4

Evaluation of the ARCHITECT ® Toxo IgG Avidity Assay on Samples from Group 2 and Group 3

| | | Vidas Toxo IgG Avidity | | | |
|---|---|---|---|---|---|
| | | LOW | EQV | HIGH | TOTAL |
| ARCHITECT ® Toxo IgG Avidity | LOW | 23 | 0 | 0 | 23 |
| | EQV | 0 | 0 | 0 | 0 |
| | HIGH | 0 | 1 | 23 | 24 |
| | TOTAL | 23 | 1 | 23 | 47 |

ARCHITECT ®/Vidas Relative Agreement: 46/46 = 100%
Vidas (BioMerieux SA, Lyon, France)

As can be seen from Table 4, the ARCHITECT® and Vidas (BioMérieux SA, Lyon, France) assays are in excellent agreement with one another, i.e., samples with low and high avidity results in the ARCHITECT® assay also have corresponding low and high avidity results, respectively, in the Vidas assay (BioMérieux SA, Lyon, France). The correlation between the ARCHITECT® and Vidas Toxo IgG avidity assay (BioMérieux SA, Lyon, France) results was evaluated across samples from Groups 2 and 3 (n=47) and a correlation coefficient of r=0.97 was obtained. This was a surprising and unexpected result for two reasons: first, the avidity assays are qualitative and hence quantitative agreement would not necessarily be expected; and second, they use very different assay formats, i.e., the competitive antigen format selectively removes high avidity IgG from the patient sample whereas the chaotropic format removes low avidity IgG in a wash step.

There are several advantages of the competitive antigen format of the ARCHITECT® Toxo IgG avidity over the chaotropic format of other Toxo IgG avidity assays. First, no chaotropic reagents are required to perform the assay. Chaotropic reagents can be hazardous or corrosive to an automated immunoassay instrument platform and may also cross-contaminate other assays thereby causing aberrant results. Second, it is known that the Avidity Index is affected to some extent by the anti-human IgG concentration against an infectious agent (Hedman, K. and Seppala, I., supra). Most conventional avidity assays employing chaotropic reagents do not compensate for this effect whereas the present invention utilizes a series of dilution protocols to dilute samples in the appropriate range, thus ensuring that the Avidity Index result is not confounded by the anti-IgG titer present in patient samples.

Given the excellent agreement between the chaotropic method and the competitive antigen method of the present invention for the determination of antibody avidity, additional applications of the methods of the present invention are possible. For example, in addition to HCMV and T. gondii, the chaotropic method has been useful to discriminate between acute infection and infections acquired in the distant past for many infectious diseases. It is believed that the competitive antigen method described herein could also be used at the diagnostic level to discriminate between acute and chronic infection for a variety of diseases, including those for which the chaotropic method has not been described. Furthermore, the competitive antigen method, as was shown for HCMV, may provide superior assay performance over the chaotropic method without the accompanying drawbacks and hazards associated with the use of chaotropic reagents.

EXAMPLE 9

"Simulated" Low Avidity Controls for CMV and Toxo

Step A: Controls for Testing

The "ARCHITECT® CMV IgG High Avidity Control" described in EXAMPLE 1 contains high-titer (ca. 200 AU/ml) and high avidity CMV IgG (avidity index ca. 90%). The "ARCHITECT® Toxo IgG High Avidity Control" described in EXAMPLE 1 contains high titer (ca. 700 IU/ml) and high avidity Toxo IgG (avidity index ca. 70%).

Step B: "Simulated CMV IgG Low Avidity Control"

The ARCHITECT® CMV IgG avidity assay described in EXAMPLE 3 has four automated dilution protocols: Dilution Protocol No. 1, 5-16 AU/ml; Dilution Protocol No. 2, 16-50 AU/ml; Dilution Protocol No. 3, 50-150 AU/ml; Dilution Protocol No. 4, 150-500 AU/ml. The "ARCHITECT® CMV IgG High Avidity Control", which contains ca. 200 AU/ml, should normally be run in Dilution Protocol No. 4 in order to obtain a valid avidity result. This control was run in Dilution Protocol Nos. 1-4 with the following results.

TABLE 5

Evaluation of the ARCHITECT ® CMV IgG High Avidity Control Across All Four Dilution Protocols in the ARCHITECT ® CMV IgG Avidity Assay

| Protocol No. | Titer Range (AU/ml) | Avidity Index (%) | Interpretation |
|---|---|---|---|
| 1 | 5-16 | 30.5 | Low |
| 2 | >16-50 | 64.4 | High |
| 3 | >50-150 | 80.2 | High |
| 4 | >150-500 | 93.4 | High |

As can be seen from Table 5, the "ARCHITECT® CMV IgG High Avidity Control" "mimics" a low avidity IgG control when run incorrectly in Protocol No. 1 instead of the correct Dilution Protocol No. 4. The dilution factor in Protocol No. 1 was not sufficient for this high titer high avidity control, resulting in the high titer IgG overcoming the "blocking" by the "liquid phase antigen", and thereby binding to the "solid phase antigen". Hence, a "simulated" low avidity control for CMV IgG can simply be obtained by running the high avidity control in a dilution protocol that "under dilutes" the control in such a manner as resulting in the binding of high avidity IgG to the "solid phase antigen" and thereby registering a low avidity IgG result in the assay.

Step C: "Simulated Toxo IgG Low Avidity Control"

The ARCHITECT® Toxo IgG avidity assay described in EXAMPLE 7 has three automated dilution protocols: Dilution Protocol No. 1, 3-20 IU/ml; Dilution Protocol No. 2, 21-200 IU/ml; Dilution Protocol No. 3, 201-2000 IU/ml. The "ARCHITECT® Toxo IgG High Avidity Control", which contains ca. 700 IU/ml, should normally be run in Dilution Protocol No. 3 in order to obtain a valid avidity result. This control was run in Dilution Protocol Nos. 1-3 with the following results.

TABLE 6

Evaluation of the ARCHITECT ® Toxo IgG High Avidity
Control Across All Three Dilution Protocols in the
ARCHITECT ® Toxo IgG Avidity Assay

| Protocol No. | Titer Range (IU/ml) | Avidity Index (%) | Interpretation |
|---|---|---|---|
| 1 | 3-20 | 0.7 | Low |
| 2 | >20-200 | 11.9 | Low |
| 3 | >200-2000 | 65.1 | High |

As can be seen from Table 6, the "ARCHITECT® Toxo IgG High Avidity Control" "mimics" a low avidity IgG control when run incorrectly in Protocol No. 1 instead of the correct Dilution Protocol No. 3. The dilution factor in Protocol No. 1 was not sufficient for this high titer high avidity control, resulting in the high titer IgG overcoming the "blocking" by the "liquid phase antigen", and thereby binding to the "solid phase antigen". Hence, a "simulated" low avidity control for Toxo IgG can simply be obtained by running the high avidity control in a dilution protocol that "under dilutes" the control in such a manner as resulting in the binding of high avidity IgG to the "solid phase antigen" and thereby registering a low avidity IgG result in the assay.

The chaotropic method cannot use "simulated" low avidity controls. Thus, it is believed that the competitive antigen avidity assay of the present invention has several distinct advantages over the chaotropic method. First, high avidity IgG plasma is relatively easy to source thus ensuring that "simulated" low avidity IgG assay controls will be available to monitor avidity assay validity. Second, it will be easier to develop an avidity assay for known and new infectious diseases using the competitive antigen format than the chaotropic format, especially in cases where disease seroprevalence and incidence are low, i.e., cases where low avidity IgG patient samples or plasma for the disease of interest are unavailable or hazardous to individuals developing new avidity tests. The rapid development of diagnostic tests for newly emerging pathogens, especially the avidity assay, can be used as an aid to diagnose, treat, and quarantine individuals in the acute phase of the disease who may readily transmit the infection to naive individuals.

What is claimed is:

1. A method of distinguishing between acute and chronic infection in a human patient by determining the avidity of human anti-infectious agent IgG antibody in a sample from said patient, said patient suspected of having been infected by an infectious agent, comprising the steps of:

a) adding at least one purified antigen from said infectious agent to a liquid phase solution to create a liquid phase antigen solution, coating said at least one purified antigen onto a solid phase to create a solid phase antigen, and removing said liquid phase antigen solution from said solid phase antigen;

b) in a first assay, contacting a test sample from said patient with said liquid phase solution comprising no liquid phase antigen, c) subsequently contacting said diluted test sample, in the absence of said liquid phase antigen, with said coated solid phase of step a) for a time and under conditions sufficient for formation of antibody/antigen complexes;

d) washing said coated solid phase of step c);

e) in a second assay, contacting a test sample from said patient with liquid phase antigen solution, f) subsequently contacting said test sample/liquid phase antigen solution with said coated solid phase of step a) for a time and under conditions sufficient for formation of antibody/antigen complexes;

g) washing said contacted solid phase antigen of step f);

h) adding a conjugate to said first and second assays for a time and under conditions sufficient for formation of anti-IgG/antibody/antigen complexes in said first and second assays, wherein said conjugate comprises an anti-IgG antibody attached to a signal-generating compound capable of generating a detectable signal;

i) detecting a signal generated by said signal-generating compound in said first and second assays;

j) determining the ratio between said signal obtained in said second assay and said signal obtained in said first assay, wherein said ratio is proportional to the level of human anti-infectious agent low avidity IgG antibody present in said patient sample;

k) multiplying said ratio of step h) by 100 and subtracting said multiplied ratio from 100 in order to determine an Avidity index, an Avidity index below a first numerical value indicating said patient has low avidity anti-infectious agent IgG and an acute infection and an Avidity index above a second numerical value indicating said patient has high avidity anti-infectious IgG and a chronic infection with said infectious agent.

2. The method of claim 1 wherein said infectious agent is selected from the group consisting of a virus, a parasite, a fungus and a bacteria.

3. The method of claim 1 wherein said solid phase is selected from the group consisting a porous material, a non-porous material, a latex particle, a magnetic particle, a microparticle, a bead, a membrane, a microtiter well and a plastic tube.

4. A method of distinguishing between chronic *Toxoplasma gondii* (*T. Gondii*) and possible acute infection in a human patient by determining the avidity of human anti-*T. gondii* IgG antibody in a sample from said patient comprising the steps of:

a) adding at least one purified antigen from *T. gondii* to a liquid phase solution to create a liquid phase antigen solution, coating said at least one purified antigen onto a solid phase to create a solid phase *T. gondii* antigen, and removing said liquid phase *T. gondii* antigen solution from said solid phase *T. gondii* antigen;

b) in a first assay, contacting a test sample from said patient with said liquid phase solution comprising no liquid phase antigen, c) subsequently contacting said diluted test sample, in the absence of said liquid phase *T. gondii* antigen, with said coated solid phase *T. gondii* antigen of step a) for a time and under conditions sufficient for formation of antibody/antigen complexes;

d) washing said coated solid phase of step c);

e) in a second assay, contacting a test sample from said patient with liquid phase *T. gondii* antigen solution, f) subsequently contacting said test sample/liquid phase *T. gondii* antigen solution with said coated solid phase of step a) for a time and under conditions sufficient for formation of antibody/antigen complexes;

g) washing said contacted solid phase *T. gondii* antigen of step f);

h) adding a conjugate to said first and second assays for a time and under conditions sufficient for formation of anti-IgG/antibody/antigen complexes in said first and second assays, wherein said conjugate comprises an anti-IgG antibody attached to a signal-generating compound capable of generating a detectable signal;

i) detecting a signal generated by said signal-generating compound in said first and second assays;

j) determining the ratio between said signals obtained in said second assay and said signal obtained in said first assay, wherein said ratio is proportional to the level of human anti-*T. gondii* low avidity IgG antibody present in said patient sample;

k) multiplying said ratio of step h) by 100 and subtracting said multiplied ratio from 100 in order to determine an Avidity index, an Avidity index of less than 20% indicating said patient has low avidity anti-*T. gondii* IgG and may or may not have an acute *T. gondii* infection whereas an Avidity index greater than 50% indicating said patient has high avidity anti-*T. gondii* IgG and a chronic *T. gondii* infection.

5. The method of claim 4 wherein said at least one purified antigen is selected from the group consisting of P22, P24, P25, P28, P29, P30, P35, P41, P54, P66 and P68.

6. The method of claim 4 wherein said patient sample is pretreated with a solution prior to addition of said coated solid phase.

7. The method of claim 4 wherein said solid phase is selected from the group consisting a porous material, a non-porous material, a latex particle, a magnetic particle, a microparticle, a bead, a membrane, a microtiter well and a plastic tube.

8. A method of distinguishing between chronic cytomegalovirus (hCMV) and possible acute hCMV infection in a human patient by determining the avidity of human anti-hCMV IgG antibody in a sample from said patient comprising the steps of:

a) adding at least one purified antigen from hCMV to a liquid phase solution to create a liquid phase antigen solution, coating said at least one purified antigen onto a solid phase to create a solid phase hCMV antigen, and removing said liquid phase hCMV antigen solution from said solid phase hCMV antigen;

b) in a first assay, contacting a test sample from said patient with said liquid phase solution comprising no liquid phase hCMV antigen, c) subsequently contacting said diluted test sample, in the absence of said liquid phase hCMV antigen, with said coated solid phase of step a) for a time and under conditions sufficient for formation of antibody/antigen complexes;

d) washing said coated solid phase of step c);

e) in a second assay, contacting a test sample from said patient with liquid phase hCMV antigen solution, f) subsequently contacting said test sample/liquid phase hCMV solution with said coated solid phase of step a) for a time and under conditions sufficient for formation of antibody/antigen complexes;

g) washing said contacted solid phase hCMV antigen of step f);

h) adding a conjugate to said first and second assays for a time and under conditions sufficient for formation of anti-IgG/antibody/antigen complexes in said first and second assays, wherein said conjugate comprises an anti-IgG antibody attached to a signal-generating compound capable of generating a detectable signal;

i) detecting a signal generated by said signal-generating compound in said first and second assays;

j) determining the ratio between said signal obtained in said second assay and said signal obtained in said first assay, wherein said ratio is proportional to the level of human anti-hCMV low avidity IgG antibody present in said patient sample;

k) multiplying said ratio of step h) by 100 and subtracting said multiplied ratio from 100 in order to determine an Avidity index, an Avidity index of less than 40% indicating said patient has low avidity anti-hCMV IgG and may or may not have an acute hCMV infection whereas an Avidity index greater than 70% indicating said patient has high avidity anti-hCMV IgG and a chronic hCMV infection.

9. A method of distinguishing between chronic cytomegalovirus (hCMV) and possible acute hCMV infection in a human patient by determining the avidity of human anti-hCMV IgG antibody in a sample from said patient comprising the steps of:

a) adding at least one purified antigen from hCMV to a liquid phase solution to create a liquid phase hCMV antigen, coating said at least one purified hCMV antigen onto a solid phase to create a solid phase hCMV antigen, and removing said liquid phase hCMV antigen solution from said solid phase hCMV antigen;

b) in a first assay, contacting a test sample from said patient with liquid phase solution comprising no liquid phase antigen, c) subsequently contacting said diluted test sample, in the absence of said liquid phase hCMV antigen, with said coated solid phase of step a) for a time and under conditions sufficient for formation of antibody/antigen complexes;

d) washing said coated solid phase of step c);

e) in a second assay, contacting a test sample from said patient with liquid phase hCMV antigen solution, f) subsequently contacting said test sample/liquid phase hCMV antigen solution with said coated solid phase of step a) for a time and under conditions sufficient for formation of antibody/antigen complexes;

g) washing said contacted solid phase antigen of step f);

h) adding a conjugate to said first and second assays for a time and under conditions sufficient for formation of anti-IgG/antibody/antigen complexes in said first and second assays, wherein said conjugate comprises an anti-IgG antibody attached to a signal-generating compound capable of generating a detectable signal;

i) detecting a signal generated by said signal-generating compound in said first and second assays;

j) determining the ratio between said signal obtained in said second assay and said signal obtained in said first assay, wherein said ratio is proportional to the level of human anti-hCMV low avidity IgG antibody present in said patient sample;

k) multiplying said ratio of step h) by 100 and subtracting said multiplied ratio from 100 in order to determine an Avidity index, an Avidity index of less than 50% indicating said patient has low avidity anti-hCMV IgG and may or may not have an acute hCMV infection whereas an Avidity index greater than 60% indicating said patient has high avidity anti-hCMV IgG and a chronic hCMV infection.

10. The method of claim 8 or claim 9 wherein said at least one purified antigen is selected from the group consisting of pp38, pp53, pp65, p130 and pp150.

11. The method of claim 8 or claim 9 wherein said patient sample is pretreated with solution prior to addition of said coated solid phase.

12. The method of claim 8 or claim 9 wherein said solid phase is selected from the group consisting a porous material, a non-porous material, a latex particle, a magnetic particle, a microparticle, a bead, a membrane, a microtiter well and a plastic tube.

* * * * *

UNITED STATES PATENT AND TRADEMARK OFFICE
CERTIFICATE OF CORRECTION

PATENT NO.         : 7,432,046 B2                                Page 1 of 1
APPLICATION NO. : 11/265481
DATED              : October 7, 2008
INVENTOR(S)        : Gregory T. Maine et al.

It is certified that error appears in the above-identified patent and that said Letters Patent is hereby corrected as shown below:

Column 8, line 50, "a bead, a membrane, and a microtiter well or" to read as --a bead, a membrane, a microtiter well or--

Column 15, line 16, "The viral antigen supernatant,was" to read as --The viral antigen supernatant was--

Column 17, line 15, "viral ant igen present" to read as --viral antigen present--

Column 28, line 32, Claim 3: "selected from the group consisting a porous material," to read as --selected from the group consisting of a porous material,--

Column 29, line 27, Claim 7: "selected from the group consisting a porous material," to read as --selected from the group consisting of a porous material,--

Column 31, line 5, Claim 12: "selected from the group consisting a porous material," to read as --selected from the group consisting of a porous material,--

Signed and Sealed this

Twenty-second Day of June, 2010

David J. Kappos
*Director of the United States Patent and Trademark Office*